United States Patent
Welz et al.

(10) Patent No.: US 11,759,505 B2
(45) Date of Patent: Sep. 19, 2023

(54) PREPARING AND USE OF GLU-PLASMINOGEN FROM BLOOD FRACTIONS

(71) Applicant: PREVIPHARMA CONSULTING GMBH, Mannheim (DE)

(72) Inventors: Ricarda Welz, Mauer (DE); Hanne Rieke Gerding, Mannheim (DE); Marc Mazur, Weinheim (DE); Stephan T. Kiessig, Wiesloch (DE); Hermann E. Karges, Marburg (DE)

(73) Assignee: PREVIPHARMA CONSULTING GMBH, Mannheim (DE)

( * ) Notice: Subject to any disclaimer, the term of this patent is extended or adjusted under 35 U.S.C. 154(b) by 555 days.

(21) Appl. No.: 16/491,408

(22) PCT Filed: Mar. 9, 2018

(86) PCT No.: PCT/EP2018/055984
§ 371 (c)(1),
(2) Date: Sep. 5, 2019

(87) PCT Pub. No.: WO2018/162754
PCT Pub. Date: Sep. 13, 2018

(65) Prior Publication Data
US 2020/0016246 A1  Jan. 16, 2020

(30) Foreign Application Priority Data

Mar. 9, 2017 (EP) .................................. 17160106

(51) Int. Cl.
*C12N 9/68* (2006.01)
*A61K 38/48* (2006.01)
*C12P 21/00* (2006.01)

(52) U.S. Cl.
CPC .......... *A61K 38/484* (2013.01); *C12N 9/6435* (2013.01); *C12P 21/00* (2013.01); *C12Y 304/21007* (2013.01)

(58) Field of Classification Search
CPC .............. A61K 38/484; C12N 9/6435; C12Y 304/21007
See application file for complete search history.

(56) References Cited

U.S. PATENT DOCUMENTS

| | | |
|---|---|---|
| 5,288,489 A | 2/1994 | Reich et al. |
| 2003/0124703 A1* | 7/2003 | Nur ................ C12Y 304/21007 435/217 |
| 2010/0145021 A1 | 6/2010 | Marguerre |
| 2014/0205588 A1 | 7/2014 | Zwaal |
| 2015/0344861 A1* | 12/2015 | Kumar .................. C07K 16/40 424/94.67 |

FOREIGN PATENT DOCUMENTS

| | | |
|---|---|---|
| CN | 101605813 A | 12/2009 |
| GB | 1305504 A | 2/1973 |
| JP | H08-291080 A | 11/1996 |
| JP | H08291080 A * | 11/1996 |
| JP | 2014525235 A | 9/2014 |
| WO | 02/095019 A1 | 11/2002 |

OTHER PUBLICATIONS

Austin and Hux, Journal or Vascular Surgery, 2002, 36:194-195.
Seitz et al. Impaired fibrinolysis and protein C increase after cadaver kidney transplantation. Thromb Res. May 1, 1986;42(3):277-88.
Boi et al., Journal of Membrane Science, 2015, 475:71-79.
Stricker, R. B.; Wong, Activation of plasminogen by tissue plasminogen activator on normal and thrombasthenic platelets: effects on surface proteins and platelet aggregation. Blood 1986, S. 275-280.
Kunamneni, A.; Durvasula, R. Streptokinase—A Drug for Thrombolytic Therapy: A Patent Review. Recent advances in cardiovascular drug discovery 2014, S. 106-121.
Takada, Akikazu; Takada, Yumiko, Activation pathway of Glu-plasminogen to Lys-plasmin by urokinase. Thrombosis research 1982, S. 671-677.
Wohl, R. C.; Kinetics of activation of human plasminogen by different activator species at pH 7.4 and 37 degrees C, The Journal of Biological Chemistry 1980, S. 2005-2013.
Fredenburgh, J. C.; Nesheim, M. E. Lys-plasminogen is a significant intermediate in the activation of Glu-plasminogen during fibrinolysis in vitro. The Journal of Biological Chemistry 1992, S. 26150-26156.
Castellino, Francis J.; Ploplis, Victoria A. Structure and function of the plasminogen/plasmin system. Thrombosis and haemostasis 2005, S. 647-654.
Summaria, L.; Spitz, F.; Arzadon, L.; Boreisha, I. G.; Robbins, K. C. Isolation and characterization of the affinity chromatography forms of human Glu- and Lys-plasminogens and plasmins. The Journal of Biological Chemistry 1976, S. 3693-3699.
Egbring R, Seitz R, Blanke H, Leititis J, Kesper HJ, Burghard R, Fuchs G, Lerch L. The proteinase inhibitor complexes (antithrombin III-thrombin, alpha-2-antiplasminplasmin and alpha-1-antitrypsin-elastase) in septicemia, fulminant hepatic failure and cardiac shock: value for diagnosis and therapy control in DIC/F syndrome. Behring Inst Mitt. Feb. 1986;(79):87-103.
Wada et al. Journal of Intensive Care, 2014, 2:15.

(Continued)

*Primary Examiner* — Allison M Fox
*Assistant Examiner* — Qing Xu
(74) *Attorney, Agent, or Firm* — RAPHAEL BELLUM PLLC

(57) ABSTRACT

The present invention relates to a method for isolating Glu-plasminogen, said method comprising the anion exchange chromatography of blood plasma or a plasma fraction comprising Glu-plasminogen. Furthermore, the present invention relates to Glu-plasminogen obtainable from the method of the present invention and its use in a method for treating a patient suffering from or being at risk of developing a disorder selected from the group consisting of organ failure, a thrombotic event, arterial obstructive disease, microcirculation, disseminated intravascular coagulation (DIC), and a combination of two or more thereof.

9 Claims, No Drawings

(56) References Cited

OTHER PUBLICATIONS

Hasegawa D, Tyler B, Edson JR. Thrombotic disease in three families with inherited plasminogen deficiency. Blood 1982; 60:213a.

Bird. The treatment of acute abscesses with human plasmin (fibrinolysin). Surgery. Jul. 1957;42(1):249-55.

Moser. Effects of intravenous administration of fibrinolysin (plasmin) in man. Circulation. Jul. 1959;20(1):42-55.

Robbins, K. C.; Boreisha, I. G.; Arzadon, L.; Summaria, L. Physical and chemical properties of the NH2-terminal glutamic acid and lysine forms of human plasminogen and their derived plasmins with an NH2-terminal lysine heavy (A) chain. The Journal of Biological Chemistry 1975, S. 4044-4047.

Barlow, G. H.; Summaria, L.; Robbins, K. C. Molecular weight studies on human plasminogen and plasmin at the microgram level. The Journal of Biological Chemistry 1969, S. 1138-1141.

Hawke and Lea: Biochem. J. Jun. 1953;54(3):475-9.

Zimmermann: J. Bacteriol., 1962, 84:1297-1302.

E. Previtali, P. Bucciarelli, S.M. Passamonti, I. Martinelli, Risk factors for venous and arterial thrombosis, Blood transfusion = Transfusione del sangue, 9 (2011) 120-138.

J. Stone, P. Hangge, Deep vein thrombosis: pathogenesis, diagnosis, and medical management, Cardiovascular diagnosis and therapy, 7 (2017) 276-284.

Prentice. Plasminogen activation and the coagulation process J.Clin. Path. 22 (1969) 367-68.

S. Gando, M. Levi, C.H. Toh, Disseminated intravascular coagulation, Nature reviews. Disease primers, 2 (2016) 16037.

Seitz, R.; Karges, H. E.; Wolf, M.; Egbring, R. Reduced fibrinolytic capacity and its restoration by plasminogen substitution in acute renal failure. International journal of tissue reactions 1989, S. 39-46.

Stoll G.: Molecular mechanisms of thrombus formation in ischemic stroke: novel insights and targets for treatment, Blood 2008, 112:3555-3562.

The National Institute of Neurological Disorders and Stroke rt-PA Stroke Study Group. Tissue plasminogen activator for acute ischemic stroke. N Engl J Med 1995;333:1581-1588.

Choi JH, Bateman BT, Mangla S, et al. Endovascular recanalization therapy in acute ischemic stroke. Stroke 2006;37:419-424.

Adams H, Adams R, del Zoppo G, Goldstein LB. Guidelines for the early management of patients with ischemic stroke. Stroke 2005;36:916-921.

Cederholm-Williams, S. Concentration of plasminogen and antiplasmin in plasma and serum. Journal of Clinical Pathology 1981, S. 979-981.

Fiessinger, Jean-Noel; Complications of intraarterial urokinase-lys-plasminogen infusion therapy in arterial ischemia of lower limbs. American Journal of Roentgenology 146(1):157-9 Feb. 1986 (revision of 1985).

Mousavi and Nikougoftar,"Preparation of Plasminogen by Affinity Chromatography", Iranian Journal of Blood and Cancer, 6(4):165-168 (2014).

\* cited by examiner

PREPARING AND USE OF GLU-PLASMINOGEN FROM BLOOD FRACTIONS

The present invention relates to a method for isolating Glu-plasminogen, said method comprising the anion exchange chromatography of blood plasma or a plasma fraction comprising Glu-plasminogen. Furthermore, the invention relates to Glu-plasminogen obtainable from the method of the present invention and its use in a method for treating a patient suffering from or being at risk of developing a disorder selected from the group consisting of organ failure, a thrombotic event, arterial obstructive disease, microcirculation, disseminated intravascular coagulation (DIC), and a combination of two or more thereof. Plasminogen according to this invention may be used also to treat patients suffering from acquired plasminogen deficiencies in general. Those patients may therefore be at risk to develop organ failure (e.g., organ failure in the patient's kidney, heart, brain, liver, lung, muscles, excretory glands, endocrine glands, eyes, bones, etc.).

Organ failure is a severe life-threatening pathologic condition. Often, multi-organ failure is caused by sepsis, polytrauma and/or virus diseases leading to shock symptoms and initiating the release of tissue factor and ending in coagulation processes. Polytrauma shock and surgery may lead to tissue damage, malignant tumors to a release of metastasis and in the case of sepsis, leucocytes are increased. Each mechanism may initiate the enhancement of tissue factors and can be associated with the formation of fibrin clots. If fibrinolysis cannot balance the hyper-coagulation, this event frequently leads to multi-organ failure. Impaired fibrinolysis and protein C increase after cadaver kidney transplantation is taught by Seitz et al. [Seitz R, Michalik R, Karges H E, Lange H, Egbring R. Impaired fibrinolysis and protein C increase after cadaver kidney transplantation. Thromb Res. 1986 May 1; 42(3):277-88].

Patients with multi-organ failure can be treated with a variety of different medicaments to find a suitable treatment strategy as fast as possible.

Patients with multi-organ failure due to sepsis are usually treated with antibiotics and with a thrombosis prophylaxis. In some cases, the patients are also treated by organ specific treatments, such as dialysis for kidney failure, surgery of multi-organ defects (e.g. appendix), ventilation therapy and anti-infective therapy for different bacteria and vascular related drugs exhibiting systemic vascular effects (catecholamines such as adrenaline, noradrenaline), hemodynamic stabilization, and activated protein C (optionally recombinant) and immunoglobulins (e.g. IgG and IgM).

Such treatments bear severe undesired side-effects. Therefore, treating a thrombotic effect by means of natural protease inhibitors has been considered. Current standard of care for a thrombotic effect does not improve the fibrinolysis by using natural protease inhibitors. Addition of natural protease inhibitors, like antithrombin-III (primary inhibiting F.Xa and thrombin) has the deficiency that existing fibrin clots are not influenced by the treatment with such natural protease inhibitors. Fibrinolysis cannot be initiated, leading to multi-organ failure.

The treatment of thromboses is usually medicated. The surgical removal of venous thrombi is reserved for special cases. In order to prevent the thrombus from enlarging, an anticoagulation inhibition is sought. Initially, heparin preparations or factor Xa inhibitors are used. When the growth of the clot stops, the body can begin to clean up the damage. He breaks down the clot and tries to get the veins free again. This takes several weeks to months—the more sections of the venous system were affected, the longer. In the breakdown of the clot and the regeneration of the veins substances are released, which increase the coagulability of the blood. During this time, the risk of a renewed thrombosis is particularly great. Therefore, further anticoagulant drugs are often avoided. Then 4-hydroxycoumarins—such as phenprocoumone, warfarin or ethylbiscoumacetat—for about three to six months may be used. The use of cumarins typically requires regular blood tests and special attention, because the drugs prevent thrombosis, but also increase the willingness to bleed. Above all, this risk of bleeding due to anticoagulant therapy is still an unsolved problem in everyday clinical practice.

Purification methods for plasminogen in general have been described in the literature (cf. GB-A 1305504).

The methods are however not satisfying, in particular as the obtained plasminogen is not stabilized and will contain fractions of Lys-plasminogen. Other methods show rather poor recovery rates and do not clearly discriminate between Glu-plasmin, Glu-plasminogen and Lys-plasminogen (cf. WO 2002/095019; U.S. Pat. No. 5,288,489; Boi et al., Journal of Membrane Science, 2015, 475:71-79).

The blood coagulation is balanced by two inhibitors, antithrombin III and heparin cofactor II. Formed fibrin clots are only removed by activation of the fibrinolytic system. The activation of the fibrinolytic system is dependent on the plasmin activation. Human plasma contains plasminogen in several forms of activation starting with Glu-plasminogen (native), Lys-plasminogen (slightly activated) and plasmin, in its activated form. The activation of the native Glu-plasminogen through uPA, tPA in a healthy individual is a key mechanism (Stricker, R. B.; Wong, Activation of plasminogen by tissue plasminogen activator on normal and thrombasthenic platelets: effects on surface proteins and platelet aggregation. Blood 1986, S. 275-280).

Streptokinase or urokinase is used in therapeutic setting to achieve a thrombolysis in different thrombogenic events (Kunamneni, A.; Durvasula, R. Streptokinase-A Drug for Thrombolytic Therapy: A Patent Review. Recent advances in cardiovascular drug discovery 2014, S. 106-121; Takada, Akikazu; Takada, Yumiko, Activation pathway of Glu-plasminogen to Lys-plasmin by urokinase. Thrombosis research 1982, S. 671-677). The fibrinolysis is started due to the activation of plasminogen (PLG) leading to the cleavage from PLG to plasmin [Wohl, R. C.; Kinetics of activation of human plasminogen by different activator species at pH 7.4 and 37 degrees C., The Journal of Biological Chemistry 1980, S. 2005-2013]. Thereby three different activation mechanisms are known [Fredenburgh, J. C.; Nesheim, M. E. Lys-plasminogen is a significant intermediate in the activation of Glu-plasminogen during fibrinolysis in vitro. The Journal of Biological Chemistry 1992, S. 26150-26156]. Plasminogen has a high binding affinity to endothelia cells and fibrin clots. The additional binding of tissue plasminogen activator (tPA) leads to an activation and plasmin formation. The last mechanism is illustrated by a binding of plasminogen on cell surface, which is activated by tPA to plasmin [Stricker, R. B.; Wong, Activation of plasminogen by tissue plasminogen activator on normal and thrombasthenic platelets: effects on surface proteins and platelet aggregation. Blood 1986, S. 275-280].

The activated plasmin is a key enzyme in the fibrinolytic system. Thus, as long as plasmin is bound to fibrin clot matrix it is not inhibited by the control inhibitor alpha-2-antiplasmin (A2AP), but released plasmin is instantaneously inhibited. Free plasmin has a very short half-life period of 0.1 sec. The half-life period of Glu-plasminogen and alpha-2-antiplasmin (A2AP) are 50 hr. In contrast Lys78-plasminogen has a half-life period of only 20 hr [Fredenburgh, J. C.; Nesheim, M. E. Lys-plasminogen is a significant intermediate in the activation of Glu-plasminogen during fibrinolysis in vitro. The Journal of Biological Chemistry 1992, S. 26150-26156]. Plasmin exhibits preferential cleavage at the carboxyl side of Lysine and Arginine residues with higher selectivity than trypsin. It converts polymerized fibrin into soluble products [Castellino, Francis J.; Ploplis, Victoria A. Structure and function of the plasminogen/plasmin system. Thrombosis and haemostasis 2005, S. 647-654].

The intermediate molecule Lys-plasminogen typically exists only at the point of fibrin clots in the human body. Lys-plasminogen is typically directly transformed to plasmin after the conversion from Glu- to Lys-plasminogen. Hence, Lys-plasminogen, the pre-activated form of plasminogen, does typically not circulate in the human body.

In the human body, a ratio of decreased A2AP (alpha-2-antiplasmin) (70-80%) and PLG increased by 100% can be measured. The PLG concentration in the human serum is ca. 0.2 g/L with a plasminogen reference activity in the range of from 0.75 to 1.60 U/mL [Cederholm-Williams, S. Concentration of plasminogen and antiplasmin in plasma and serum. Journal of Clinical Pathology 1981, S. 979-981]. The molecular weight of PLG is 92 kDa [Summaria, L.; Spitz, F.; Arzadon, L.; Boreisha, I. G.; Robbins, K. C. Isolation and characterization of the affinity chromatography forms of human Glu- and Lys-plasminogens and plasmins. The Journal of Biological Chemistry 1976, S. 3693-3699]. Under certain pathological conditions, A2AP>PLG (average ratio of 1.26) leads to an irreversible repulsion. Deficiency of plasminogen leading to the danger of undesired persistence of fibrin clots, especially in the microvasculature.

As illustrated in the example section, it could be evidenced that in different states of a disease, patients show an acquired plasminogen deficiency.

In some cases, the increased concentration of alpha-2-antiplasmin inhibits the optional usable amount of plasminogen. But in other cases, the alpha-2-antiplasmin concentration had no influence in the decreased fibrinolysis. These patients have already used up most of the amount of plasminogen. The resulting deficiency of plasminogen cannot be balanced by the human body due to the lack of reproduction. The sensible balance of coagulation and fibrinolytic system shifts to hypercoagulation. This is also the reason why the administration of tissue plasminogen activator may show only an improvement in 30% of the patients with a stroke.

Summarized, earlier studies have shown that the administration of compositions comprising plasminogen in general can improve the physical conditions of a patient suffering from extraordinary low (overall) levels of plasminogen in its blood. Decreased plasminogen levels can be caused by an increased consumption of this protein. For instance, patients with organ failure show a rather low level of plasminogen in their blood. Glu-plasminogen has been tested for orphan drug status of plasminogen deficiency without knowing a specific field of activity.

The orphan drug status was reached only for the plasminogen deficiency hereditary. These patients have interestingly no increased hypercoagulation in a healthy state. For this indication, plasminogen is mostly used to prevent severe clinical manifestations primarily related to the formation of fibrous depositions on mucous membranes throughout the body but not primary a thrombotic event.

In principle, the recovery of a patient with multi-organ failure including multiple skin necrosis due to *Neisseria meningitides* using Glu-plasminogen as a treatment illustrates a high potential as a biopharmaceutical. Data of recovery of a 4 years old boy from multiple skin necrosis (Waterhouse Friderichsen Syndrome) [Egbring R, Seitz R, Blanke H, Leititis J, Kesper H J, Burghard R, Fuchs G, Lerch L. The proteinase inhibitor complexes (antithrombin III-thrombin, alpha-2-antiplasmin-plasmin and alpha-1-antitrypsin-elastase) in septicemia, fulminant hepatic failure and cardiac shock: value for diagnosis and therapy control in DIC/F syndrome. Behring Inst Mitt. 1986 February; (79): 87-103]. Data of a patient with *Neisseria meningitides* illustrate the recovery by Glu-plasminogen treatment visible by increasing urine excretion.

The patient survived and could be released of intensive care after 23 days of plasminogen treatment. Dis-seminated intravascular coagulation (DIC) is also described in Wada et al. (Journal of Intensive Care, 2014, 2:15).

It has been surprisingly found that Glu-plasminogen has a significantly higher desirable activity than the matured form Lys-plasminogen or plasmin. The practical usability of Glu-plasminogen is however still limited by its poor availability. There are few satisfying methods, such as fractionation processes, for isolating the Glu-plasminogen known in the art.

Thus, efficient methods for obtaining and isolating Glu-plasminogen, in particular at a large scale and quantity with reproducible processes, are desirable.

In the view of the above, there is still an unmet need for efficient methods for obtaining and isolating Glu-plasminogen. Purified Glu-plasminogen also enables further perspectives in treatments of patients such as in treating a patient suffering from or being at risk of developing organ failure and to obtain such compounds from blood fractions.

The Glu-plasminogen is the natural circulation isoform in the human plasma. Glu-plasminogen can be cleaved into Lys-plasminogen due to different isolation and purification processes. The thrombotic disease, hereditary plasminogen deficiency, was looked at in the year 1982 [Hasegawa D, Tyler B, Edson J R. *Thrombotic disease in three families with inherited plasminogen deficiency. Blood* 1982; 60: 213a.]. In the beginning many researchers attempted to treat these patients with Lys-plasminogen injections, which resulted in enormous side effects such as bleeding. The patients developed groin hematoma, embolies and macroscopic meaturia [Jean-Noel Fiessinger_1985_Complication of Intraarterial Urokinase-Lys-plasminogen Infusion Therapy in Arterial Ischemia lower limbs]. The Lys-plasminogen form has another conformation and has a higher affinity to epithelia cells than the natural occurring Glu-plasminogen. The increased affinity leads to an unspecific binding of Lys-plasminogen. The bound-molecule is directly converted into plasmin, which cuts also epithelia cells. The adverse effects were higher than the positive effect of the treatment of hereditary plasminogen deficiency. The random and imprecise treatment opportunity leads to a product failure of Lys-plasminogen.

Early experiments have shown that the intravenous injection of plasmin resulted in highly adverse effects in form of bleeding. Plasmin was used seldom for the reduction of a thrombotic event on the point of care, locally during a surgery for example (BIRD F, CLIFFTON E E.: The treatment of acute abscesses with human plasmin (fibrinolysin). Surgery. 1957 July; 42(1):249-55; MOSER K M.: Effects of intravenous administration of fibrinolysin (plasmin) in man. Circulation. 1959 July; 20(1):42-55). However, it is not possible to dissolve micro thrombotic event with the direct injection of plasmin. The branched micro coagulation is only possible to reach with an intravenous injection of Glu-plasminogen. When Glu-plasminogen reaches micro coagulation of fibrin clots, Glu-plasminogen is activated on the point of care and plasmin resolves the thrombus.

A minimal amount of Lys-plasminogen is enough to convert the rest of Glu-plasminogen into Lys-plasminogen and finally to plasmin. Additionally, the yield of Glu-plasminogen is dramatically reduced when a few molecules were transformed to Lys-plasminogen, due to sensible auto-activation mechanism. Therefore, the right choice of the best and sensible purification mechanism may have a considerable impact.

Surprisingly, it has been found in the experiments performed that Glu-plasminogen can be easily obtained from blood plasma and plasma fractions, in particular cryo-poor plasma, and may serve as an effective pharmaceutical agent for treating a patient suffering from or being at risk of developing organ failure.

Accordingly, a first aspect of the present invention relates to a method for isolating Glu-plasminogen, said method comprising the following steps:
(i) providing blood plasma or a plasma fraction comprising Glu-plasminogen;
(ii) contacting the blood plasma or a plasma fraction with an anion exchanger based on a resin comprising cationic groups;
(iii) washing the anion exchanger obtained from step (ii) loaded with the blood plasma or a plasma fraction with a first buffer B1 not comprising cations competing with the cationic groups of the resin of the anion exchanger;
(iv) eluating the Glu-plasminogen from the washed anion exchanger of step (iii) with a second buffer B2 comprising cations competing with the cationic groups of the resin of the anion exchanger, thereby obtaining a solution comprising buffer B2 and Glu-plasminogen;
(v) optionally adjusting the pH of the solution obtained from step (iv) to a pH in a desired range;
(vi) optionally stabilizing the Glu-plasminogen by adding one or more stabilizers that prevent the Glu-plasminogen from maturing into plasmin or Lys-plasminogen to the solution obtained from any of steps (iv), (v) or (vii);
(vii) optionally subjecting the solution from any of steps (iv) to (vi) to one or more antiviral treatments; and
(viii) optionally drying or freeze drying the solutions comprising Glu-plasminogen obtained from any of steps (iv) or (vii).

This method enables to obtain comparably high yields of rather pure Glu-plasminogen (typically with a purity >90% (w/w) of all polypeptide components) from different plasma fractions from existing plasma fractionation processes. In comparison to processes known in the art, the process of the present invention enables to obtain increased protein yields and to minimize the Glu-plasminogen activation (into Lys-plasminogen or plasmin) with high overall protein purity.

The method of the present invention may be integrated into existing plasma fractionation process. Starting plasma intermediates include plasma, cryo-poor plasma, the flow through after captured Glu-plasminogen may flow directly into the Cohn process. Furthermore, the resulting waste fraction of paste I+II+III (i.e., I–III) or paste I+III (also: fraction I+II+III or fraction I+IIII, respectively) after the Cohn process can be used.

Any and each Cohn fraction may be used, which contains Glu-plasminogen such as, e.g., paste I, paste I+III, paste I+II+III and several intermediates. Most preferably, a fraction is used in which existing products (e.g. IgG, albumin) are not impacted by the process. After the purification of a main product. this waste fraction is usually discarded. The challenge is to keep the Glu-plasminogen form and maintaining an acceptable protein yield. This is generally the main challenge, to figure out a profitable process with high yield, high stable product and with a minimal intervention into the standard process of a typical plasma fractionation process as defined by Cohn or Kistler-Nitschmann.

The method of the present invention allows isolating Glu-plasminogen from various plasmin fractions, including fractions that are considered as a waste fraction in the plasma fractioning procedures in the art.

As used herein, "isolating" may be understood interchangeably with "purifying" in the broadest sense as increasing the content of the isolated Glu-plasminogen in the composition. It does not necessarily be pure. However, preferably, the product of the process comprises at least 25% (w/w), based on the total protein weight, of Glu-plasminogen. More preferably, the product of the process comprises at least 50% (w/w), even more preferably at least 70% (w/w), even more preferably at least 80% (w/w), in particular at least 90% (w/w), based on the total protein weight, of Glu-plasminogen.

The purity of a Glu-plasminogen-containing sample is typically increased when conducting the method of the present invention. Purity can be increased further upon using further purification steps. Product specifications mean that Glu-plasminogen is purified at a high purity. Impurities (e.g., in the used blood plasma, the used plasma fraction, and remaining in the product) may, for example, include IgG, IgM, albumin and/or other plasma proteins. Preferably, activated proteases are (essentially) removed by the method of the present invention. Preferably, the content of Lys-plasminogen in the final product is considerably low (e.g., below 0.5%, preferably below 0.1%, more preferably below 0.05%, in particular below 0.01%), based on the total protein weight) in particular (essentially) not detectable.

Glu-plasminogen obtained by the method of the present invention may also be stabilized in the Glu-plasminogen form (i.e., does, for instance, (essentially) not convert into the Lys-plasminogen form). Minimal conversions from Glu- to Lys-plasminogen can destabilize the product. A (main) impurity in the final product is most preferably albumin, which may lead to a higher stability as well.

In a preferred embodiment, Glu-plasminogen has a purity of at least 95% or more in the final product.

In a preferred embodiment, the method of the present invention further comprises the step of diafiltration of a solution obtained from any of steps (v) to (viii) of the method of the present invention, preferably a further step of diafiltration of a solution obtained from step (v), in particular wherein said further step is a diafiltration into a glycine buffer. This step may be used to reach a high stability of the Glu-plasminogen product. The product of such further step may be a solution that is further subjected to any of steps ((v) to (viii), in particular any of steps (vi) to (viii).

Purity and stability of the Glu-plasminogen product obtained by the method of the present invention is surprisingly beneficial in comparison to that of the prior art.

The purified Glu-plasminogen obtainable by the method of intervention may preferably be diafiltrated (e.g., into glycine buffer). This additional step demonstrated a particularly highly stable Glu-plasminogen product with no proteolytic activity, no aggregates, no fragments and a high Glu-plasminogen recovery.

The terms "protein", "polypeptide" and "peptide" may be understood interchangeably throughout the invention in the broadest sense as any chemical entity mainly composed of amino acid residues and comprising at least twenty amino acid residues consecutively linked with another via amide bonds. It will be understood that a protein in the sense of the present invention may or may not be subjected to one or more posttranslational modification(s) and/or be conjugated with one or more non-amino acid moiety/moieties. The termini of the protein may, optionally, be capped by any means known in the art, such as, e.g., amidation, acetylation, methylation, acylation.

Posttranslational modifications are well-known in the art and may be but may not be limited to lipidation, phosphorylation, sulfatation, glycosylation, truncation, oxidation, reduction, decarboxylation, acetylation, amidation, deamidation, disulfide bond formation, amino acid addition, cofactor addition (e.g., biotinylation, heme addition, eicosanoid addition, steroid addition) and complexation of metal ions, non-metal ions, peptides or small molecules and addition of iron-sulphide clusters. Moreover, optionally, co-factors, in particular cyclic guanidinium monophosphate (cGMP), but optionally also such as, e.g., ATP, ADP, $NAD^+$, $NADH+H^+$, $NADP^+$, $NADPH+H^+$, metal ions, anions, lipids, etc. may be bound to the protein, irrespective on the biological influence of these co-factors.

In the context of Glu-plasminogen in particular glycosylation may play a role. An advantage of the method of the present invention is that two glycosylation patterns of Glu-plasminogen may be observable in the purified product.

Glu-plasminogen in the sense of the present invention may be Glu-plasminogen of any species of interest. Preferably, Glu-plasminogen is of human or mammalian origin, in particular is human Glu-plasminogen. Glu-plasminogen (i.e., native-intact human plasminogen) is a 291-amino acid glycoprotein with as many as 24 disulfide bonds.

Glu-plasminogen contains a single N-linked sialylated biantennary glycan. The two O-glycans possess a Gal β-1-3GalNAc core which is α-2-3 sialylated at the terminal Gal. An additional disialylated form has a second sialic acid residue with a α-2-6 linkage to GalNAc. Mono- and disialylated forms occur at a molar ratio of 80:20 in human plasminogen. The optimal conditions for human plasminogen activators are at 37° C. pH 7.4 [Wohl, R. C.; Summaria, L.; Robbins, K. C. Kinetics of activation of human plasminogen by different activator species at pH 7.4 and 37 degrees C. The Journal of Biological Chemistry 1980, S. 2005-2013]. The concentration of PLG in plasma (2.2 µM) is more than 50% occupancy of the receptor in plasma and interstitial fluid. PLG receptors are abundant on cell surfaces (37,000 sites/platelet→$10^7$ sites/endothelial cell) and are not limited to a single class of molecules. Plasmin has a molecular weight of 83 kDa [Robbins, K. C.; Boreisha, I. G.; Arzadon, L.; Summaria, L. Physical and chemical properties of the NH2-terminal glutamic acid and lysine forms of human plasminogen and their derived plasmins with an NH2-terminal lysine heavy (A) chain. The Journal of Biological Chemistry 1975, S. 4044-4047; Barlow, G. H.; Summaria, L.; Robbins, K. C. Molecular weight studies on human plasminogen and plasmin at the microgram level. The Journal of Biological Chemistry 1969, S. 1138-1141]. The free plasmin has a half-life period of 0.1 sec. contrasting the corresponding inhibitor alpha-2-antiplasmin (A2AP) has a half-life period of 2.6 days.

As is well-known, Glu-plasminogen may be cleaved and thereby matured enzymatically into Lys-plasminogen (typically cleavage N-terminally to amino acid moiety Lys77 of Glu-plasminogen), into Glu-plasmin (typically cleavage between amino acid moieties Arg561 and Val562 of Glu-plasminogen) and into (Lys-) plasmin (typically cleavage N-terminally to amino acid moiety Lys77 between amino acid moieties Arg561 and Val562 of Glu-plasminogen).

The cleavage N-terminally to amino acid moiety Lys77 of Glu-plasminogen may be facilitated by tissue plasminogen activator (tPa). The cleavage between amino acid moieties Arg561 and Val562 of Glu-plasminogen may be facilitated autocatalytically by plasmin.

Blood plasma (also designated as "plasma", "plasm" or "blood plasm" etc.) may be obtained from any source. It may for instance be obtained from a blood preservation from which the cells have been removed from. Blood plasma is also commercially available from various suppliers.

In the context of the present invention, in particular steps (i) and (ii) thereof, the term "plasma fraction" may be understood in the broadest sense as any part separated from blood plasma that comprises Glu-plasminogen. The person skilled in the art knows several routs for preparing plasma fractions from blood plasma. One commonly known example is the Cohn process (also designated as Cohn method) based on freeze-thaw cycles and gradually increasing the concentration of ethanol in the solution.

The step (v) of adjusting the pH of the solution obtained from step (iv) to a pH in a desired range may be adjusting the pH of the solution obtained from step (iv) to a pH in the range of from 4.5 to 10.3.

For example, the step (v) of adjusting the pH of the solution obtained from step (iv) to a pH in a desired range may be adjusting the pH of the solution obtained from step (iv) to a pH in the range of from 7 to 8, of from 4.5 to 5.5, of from 5.5 to 6.5, of from 6.5 to 7.3, of from 7.3 to 8.0, or of from 8.0 to 10.3.

In a preferred embodiment, step (v) is adjusting the pH of the solution obtained from step (iv) to a pH in the range of from 7 to 8 or of from 4.5 to 5.5, in particular in the range of from 7 to 8. This is a range in or near the physiological range.

In an alternative preferred embodiment, step (v) is adjusting the pH of the solution obtained from step (iv) to a pH in the range of from 4.5 to 5.5, of from 5.5 to 6.5, of from 6.5 to 7.3, of from 7.3 to 8.0, or of from 8.0 to 10.3. Such pH values may stabilize the Glu-plasminogen and optionally other ingredients.

Any of the solutions may optionally be filtered.

It will be understood that each of the procedural steps (ii)-(viii) may be optionally repeated.

Accordingly, a preferred embodiment of the present invention refers to the method comprising the following steps:
(i) providing blood plasma or a plasma fraction comprising Glu-plasminogen;
(ii) contacting the blood plasma or a plasma fraction with an anion exchanger based on a resin comprising cationic groups;
(iii) washing the anion exchanger obtained from step (ii) loaded with the blood plasma or a plasma fraction with a first buffer B1 not comprising cations competing with the cationic groups of the resin of the anion exchanger;
(iv) eluating the Glu-plasminogen from the washed anion exchanger of step (iii) with a second buffer B2 comprising cations competing with the cationic groups of the resin of the anion exchanger, thereby obtaining a solution comprising buffer B2 and Glu-plasminogen;
(v) optionally adjusting the pH of the solution obtained from step (iv) to a pH in a desired range;
(vi) stabilizing the Glu-plasminogen by adding one or more stabilizers that prevent the Glu-plasminogen from maturing into plasmin or Lys-plasminogen to the solution obtained from any of steps (iv), (v) or (vii);
(vii) subjecting the solution from any of steps (iv) to (vi) to one or more antiviral treatments, in particular wherein said antiviral treatment is:
  (vii-I) adding one or more detergents, preferably one or more detergents selected from the group consisting of Tween-20, Tween-80 and Triton-X-100, and one or more other antiviral agents such as a phosphate ester, in particular tri-n-butyl-phosphate; and
  (vii-II) removing the solution of step (vii-I);
(ii*) contacting the solution obtained from step (vii) with an anion exchanger based on a resin comprising cationic groups;
(iii*) washing the anion exchanger obtained from step (ii*) loaded with the blood plasma or a plasma fraction with a first buffer B1 not comprising cations competing with the cationic groups of the resin of the anion exchanger;
(iv*) eluating the Glu-plasminogen from the washed anion exchanger of step (iii) with a second buffer B2 comprising cations competing with the cationic groups of the resin of the anion exchanger, thereby obtaining a solution comprising buffer B2 and Glu-plasminogen;
(vii) subjecting the solution from any of steps (iv) to (vi) to one or more antiviral treatments, in particular wherein said antiviral treatment is:
  (vii-III*) ultrafiltration, in particular nanofiltration;
(v*) optionally adjusting the pH of the solution obtained from step (vii*) to a pH in a desired range (as described above, in one preferred embodiment, for example, a pH in the range of from 7 to 8 or of from 4.5 to 5.5, in particular in the range of from 7 to 8);
(vi*) optionally stabilizing the Glu-plasminogen by adding one or more stabilizers preventing the Glu-plasminogen from maturing into plasmin or Lys-plasminogen to the solution obtained from step (v*), in particular wherein said stabilizers are selected from the group consisting of aprotinin, alpha-2-antiplasmin (A2AP), D-phenylalanyl-L-prolyl-arginine chloromethyl ketone, small molecule stabilizers, and combinations thereof; and
(viii) optionally drying or freeze drying the solutions comprising Glu-plasminogen obtained from any of steps (vii*), (v*) or (vi*), in particular by freeze-drying.

Sub-step (vii-II) of removing the solution of step (vii-I) may be performed by washing with any suitable buffer. Exemplarily, an acetate buffer of 10-250 mM acetate and a pH in the range of from 5.4-7.4 may be used such a, e.g., 25 mM acetate buffer pH 5.75.

In a preferred embodiment, the plasma fraction is selected from the group consisting of:
(a) cryo-poor plasma, typically obtained from the supernatant of blood plasma subjected to being frozen and subsequently thaw;
(b) a waste fraction of paste I+II+III or I+III of the Cohn or Kistler-Nitschmann process or a combination of two or all three of these fractions; and
(c) paste I+II+III or paste I+III of the Cohn or Kistler-Nitschmann process or any fraction or waste fraction thereof containing Glu-plasminogen.

In a more preferred embodiment, the plasma fraction is selected from the group consisting of:
(a) cryo-poor plasma, typically obtained from the supernatant of blood plasma subjected to being frozen and subsequently thaw; and
(b) a waste fraction of paste I+II+III or I+III of the Cohn or Kistler-Nitschmann process or a combination of two or all three of these fractions.

In a preferred embodiment, the plasma fraction is selected from the group consisting of:
(a) cryo-poor plasma, typically obtained from the supernatant of blood plasma subjected to being frozen and subsequently thaw; and
(b) the waste fraction of paste I+II+III or paste I+III of the Cohn process or a combination of two or all three of these fractions.

The waste fraction of paste I+II+III (i.e., I–III) or paste I+III of the Cohn process is typically the pasty phase of fractions I+II+III (i.e., I–III) or I+III.

In a particularly preferred embodiment, the method of the present invention is a method for isolating Glu-plasminogen, said method comprising the following steps:
(i) providing cryo-poor plasma (including a subfraction thereof), comprising Glu-plasminogen;
(ii) contacting the cryo-poor plasma with an anion exchanger based on a resin comprising cationic groups;
(iii) washing the anion exchanger obtained from step (ii) loaded with the cryo-poor plasma with a first buffer B1 not comprising cations competing with the cationic groups of the resin of the anion exchanger;
(iv) eluating the Glu-plasminogen from the washed anion exchanger of step (iii) with a second buffer B2 comprising cations competing with the cationic groups of the resin of the anion exchanger, thereby obtaining a solution comprising buffer B2 and Glu-plasminogen;
(v) optionally adjusting the pH of the solution obtained from step (iv) to a pH in a desired range;
(vi) optionally stabilizing the Glu-plasminogen by adding one or more stabilizers that prevent the Glu-plasminogen from maturing into plasmin or Lys-plasminogen to the solution obtained from any of steps (iv), (v) or (vii);
(vii) optionally subjecting the solution from any of steps (iv) to (vi) to one or more antiviral treatments; and
(viii) optionally drying or freeze drying the solutions comprising Glu-plasminogen obtained from any of steps (iv) or (vii).

Cryo-poor plasma may be understood in the broadest sense as understood in the art. The terms "cryo poor plasma", "cryosupernatant", "cryoprecipitate depleted" may be used interchangeably therewith. It is typically understood as plasma from which the cryoprecipitate has been removed, thus, the supernatant of blood plasma subjected to being frozen and subsequently thaw.

In a preferred embodiment, step (i) of the method of the present invention is providing a plasma faction comprising Glu-plasminogen, wherein said plasma faction is paste I+III and/or from paste I+II+III or waste pastes of paste I+III and/or from paste I+II+III after caprylic acid and, optionally, calcium-triphosphate treatment.

In a preferred embodiment, step (i) of the method of the present invention is providing a plasma faction comprising Glu-plasminogen, wherein said plasma faction is the precipitate of paste I+III and/or from paste I+II+III after caprylic acid and, optionally, calcium-triphosphate treatment.

In an alternative preferred embodiment, step (i) of the method of the present invention is providing a plasma faction comprising Glu-plasminogen, wherein said plasma faction is the supernatant of paste I+III and/or from paste I+II+III after caprylic acid and, optionally, calcium-triphosphate treatment.

It will be understood that paste I+III and paste I+II+III may also be obtained from a sample previously subjected to freeze-thaw cycles (i.e., cryo-poor plasma).

Furthermore, it is possible to purify Glu-plasminogen from paste I+III and/or from (also: I–III) and, optionally, resulting waste fractions after caprylic acid and calcium-triphosphate treatment. Fraction I+II+III may be obtainable from a process for the purification of the main product IgG. In a preceding step, the paste suspension may be resolved in an acetate buffer (10 mM-250 mM, pH 5.0-6.0).

Afterwards, caprylic acid and calcium-triphostate may be added and may be removed in a depth filtration step. The filtrate may be used for further purification step of IgG and the filter cake (waste fraction) may, optionally, be washed again. Glu-plasminogen may be eluted due to specific washing steps depending on the individual fractionation process. The pH value may be adjusted. Then, the method of the present invention as described above may be conducted, thus, Glu-plasminogen may be purified.

From the paste I+III and/or from paste suspension I+II+III, Glu-plasminogen may also be directly purified. Yields of Glu-plasminogen may be minimally decreased (e.g., approximately 60 to 80 µg/mL, such as, in one example, 73 µg/mL), in comparison to plasma concentration (e.g., approximately 80 to 100 µg/mL, such as, in one example, 90 µg/mL). Exemplarily, decrease may be such that the 0.5 to 0.9fold, preferably the 0.6 to 0.8fold, in particular the 0.70 to 0.75fold, of the plasma concentration is obtained. Glu-plasminogen concentration may be higher than in the waste fraction which is often <30 µg/mL. Accordingly, in comparison to the waste fraction, Glu-plasminogen concentration may be increased at least 1.1fold, preferably at least 1.3fold, more preferably at least 1.7fold, even more preferably at least 2fold, in particular at least 2.5fold. However, significant advantages of using the waste fraction may be the additional use of otherwise discarded proteins without impacting current manufacturing procedures for protein products such as IgG. With that, a novel purification procedure is gained for a new protein product. In general, Glu-plasminogen can be isolated from paste I+III, from fraction I+II+II and the waste fraction of the Fraction I+II+III. The concentration may differ of each individual Cohn or Kistler-Nitschmann process.

In principle, the anion exchanger may be any anion exchanger suitable for the purification of a protein, in particular Glu-plasminogen, known in the art.

Typically, it will be a column, in particular a chromatographic column that bears a resin as solid phase. Most typically, the resin forms beads (mostly in the micrometer range).

Such beads may be (essentially) spherical beads of a weight average particle in the range of from 1 to 1000 µm, preferably 10 to 500 µm, more preferably 20 to 200 µm, even more preferably 50 to 150 µm, even more preferably 60 to 120 µm, in particular 70 to 100 µm.

Alternatively, also stationary filters and monolithic carriers may be used. Any solid phase may be used such as, e.g., silica, ceramics, polysaccharides or combinations of two or more thereof. The resin of the anion exchanger typically bears cationic groups or salts thereof on its surface to enable anion exchange. In the context of the present invention, such cationic groups may be any cationic groups that enable anion exchange with Glu-plasminogen without irretrievably destroying the Glu-plasminogen. A preferred resin has a high binding capacity, robust material and usability of higher flowrates. Preferably, the anion exchanger does (essentially) not modify the Glu-plasminogen, in particular does not lead to a conversion into Lys-plasminogen. Furthermore, the proteolytic activity is preferably not increased due to the usage of the anion exchanger.

In a preferred embodiment, the resin of the anion exchanger bears amino groups or salts thereof, preferably primary amino groups or salts thereof.

In a preferred embodiment, the resin of the anion exchanger bears amino groups or salts thereof, preferably primary amino groups or salts thereof, more preferably bears the structure moiety —R—$NH_2$ or —R—$NH_3^+$+$A^-$, wherein R is an organic spacer of not more than twenty carbon atoms, preferably is selected from the group consisting of a branched or unbranched $C_1$-$C_{10}$-(hetero)alkylene residue, a branched or unbranched $C_1$-$C_{10}$-(hetero)alkenylene residue, a branched or unbranched $C_1$-$C_{10}$-(hetero)alkynylene residue, a $C_4$-$C_{10}$-(hetero)cycloalkylene residue, a $C_4$-$C_{10}$-(hetero)aromatic residue, wherein all of these residues can optionally be substituted by one or more of the aforementioned residues, and $A^-$ is an anionic counterion, in particular wherein the anion exchanger bears lysyl moieties.

In a more preferred embodiment, the resin of the anion exchanger bears the structure moiety —R—$NH_2$ or —R—$NH_3^+$+$A^-$, wherein R is a $C_1$-$C_{10}$-alkylene residue and $A^-$ is an anionic counterion. In a particularly preferred embodiment, the anion exchanger bears lysyl moieties. The lysyl moieties may be L-lysyl or D-lysyl moieties, in particular L-lysyl moieties.

Preferably, the method of the present invention is also a method for reducing the proteolytic activity of the Glu-plasminogen.

The anion exchanger may have any binding capacity. In a preferred embodiment, the anion exchanger has a binding capacity of >0.1 mg plasminogen/mL drained resin, preferably >0.2 mg plasminogen/mL drained resin, more preferably >0.5 mg plasminogen/mL drained resin, even more preferably >1.0 mg plasminogen/mL drained resin, in particular >1.5 mg plasminogen/mL drained resin.

The used resin may have a high compressibility, in particular when based on ceramic beads. Accordingly, in a preferred embodiment, the solid phase of the anion exchanger bases on ceramics. For example, lysine moieties bound to ceramic beads may be used as an anion exchanger. Rapid packing of a column may be achieved when using a high density of ligand (e.g., based on lysine moieties). This may be achieved in few minutes.

For example, Lysine Hyper-D Affinity Chromatography Sorbent (commercially obtainable from Pall, USA) may be used an anion exchanger resin. Hyper-D resin, for instance, is rather rigid and allows the use of high flow rates without increased pressures or shrinking or swelling of the resin. Furthermore, the characteristics of such resin may lead to high productivity due to high binding capacity. Preferably, binding capacity is not too high in order to avoid difficulties when eluating the Glu-plasminogen and to avoid proteolytic activation mechanisms.

The anion exchanger may also be such as disclosed in the context of plasmin and plasminogen in general in any of GB-A 1305504, WO 2002/095019 or Boi et al., Journal of Membrane Science, 2015, 475:71-79.

In an alternative preferred embodiment, the solid phase of the anion exchanger bases on a polysaccharide or a combination of polysaccharides. In a more preferred embodiment, the solid phase of the anion exchanger bases on sepharose. For example, lysine moieties bound to sepharose beads may be used as an anion exchanger. Sepharose is typically based on partly crosslinked agarose. It may contain approximately 1 to 10% crosslinked agarose, preferably 2 to 5% crosslinked agarose, in particular approximately 4% crosslinked agarose. For example, ECH-Lysine Sepharose 4 Fast Flow (GE Healthcare, UK) may be used as an anion exchanger resin. This resin is based on crosslinked 4% agarose thus enables rapid processing of large sample volumes.

Any flow rate may be used. For example, a flow rate of from 10 to 5000 cm/h, preferably from 20 to 1000 cm/h, more preferably from 50 to 500 cm/h, in particular at least 200 cm/h, may be used.

In step (i), a feed volume of the blood plasma or plasma fraction is fed to the column. In a preferred embodiment, in step (i), 5 to 50 column volumes (CV), preferably 8 to 25 CV, more preferably 10 to 22 CV, even more preferably 15 to 21 CV, in particular (approximately) 20 CV, of the blood plasma or plasma fraction are used as feed.

Preferably, the contact times between the Glu-plasminogen and the anion exchanger is rather short. In one preferred embodiment, the contact time between the Glu-plasminogen and the anion exchanger is between 1 and 60 min, preferably between 2 and 45 min, more preferably between 3 and 30 min, even more preferably between 5 and 20 min, even more preferably between 7 and 15 min, in particular approximately 10 min. This contact time may also be defined as the time which a molecule of Glu-plasminogen needs to pass through the column.

Based on the contact time, the (linear) flow rate used in the method of the present invention, in particular when using a column height of 5-25 cm, may preferably be in the range of from 10 cm/h to 100 cm/h, more preferably in the range of from 20 cm/h to 80 cm/h, even more preferably in the range of from 30 cm/h to 50 cm/h, in particular in the range of from 41 cm/h to 46 cm/h.

It will be understood that the counterion $A^-$ may be any anion that is suitable for this purpose. Typically, the counterion will have a molecular weight of below 500 Da. Preferably, the counterion $A^-$ is pharmaceutically acceptable. Preferably but not necessarily, the counterion $A^-$ is selected from the group consisting of chloride, phosphate, hydrogen phosphate, bishydrogen phosphate, sulfate, hydroxyl, carbonate, and hydrogen carbonate. The counterion $A^-$ will typically such comprised in the buffers used with which the column is flushed. The counterion $A^-$ should be such that does not bind to rigidly to —R—$NH_3^+$ in order to enable rapid exchange of anions, e.g. with the anionic groups of the Glu-plasminogen.

In a preferred embodiment, the method of the present invention comprises the additional step prior to contacting the blood plasma or a plasma fraction with an anion exchanger based on a resin comprising cationic groups of step (ii):

(o) equilibrating the anion exchanger with a buffer having a pH in the range of from pH 6 to 8, in particular in the range of pH 6.5 to pH 7.4.

The buffer agent of buffer B1 and/or buffer B2 may be used at any concentration. Preferably, the concentration of the respective buffer agent of buffer B1 and/or buffer B2 is/are each independently from each other in the range of from 0.1 mM to 1 M, preferably in the range of from 1 mM to 0.5 M, in particular in the range of from 0.01 to 0.1 M. The buffer agents in both buffers B1 and B2 may be used at any concentration. Preferably, the concentration of the buffer agents in both buffers B1 and B2 are each independently from each other in the range of from 0.1 mM to 1 M, preferably in the range of from 1 M to 0.5 M, in particular in the range of from 0.01 to 0.1 M. It will be understand that, even if comparable concentrations an/or pH values may be used in B1 and B2, both buffers may comprise that same or different buffer agents and optional further ingredients.

The buffer agent of buffer B1 and/or buffer B2 may have any conductivity. Preferably, the conductivity of buffer B1 and/or buffer B2 is/are each independently from each other in the range below 500 mS/cm, preferably below 200 mS/cm, more preferably below 100 mS/cm, even more preferably in the range of from 0.1 to 50 mS/cm, even more preferably in the range of from 0.2 to 20 mS/cm, even more preferably in the range of from 0.5 to 15 mS/cm, even more preferably in the range of from 1 to 10 mS/cm, in particular approximately 5 mS/cm.

Exemplarily, phosphate buffered saline (PBS) of pH 6.6 may be used for this equilibration step. In a particularly preferred embodiment, a 0.05 M phosphate buffer pH 6.6 may be used for this equilibration step.

The pH of the buffers B1 and B2 may be each independently from each other freely chosen in the range acceptable for Glu-plasminogen, i.e., in particular not disintegrating the amide bonds thereof. It will be understood that the pH of the buffers used may be adapted to the resin of the column chosen. In particular, when a resin comprising primary amino groups is used, the pH is preferably in the basic range.

In a preferred embodiment, the first buffer B1 has a pH of 7.1 to 11.5, preferably a pH of 8.5 to 11, in particular a pH of 10 to 11. In another preferred embodiment, the second buffer B2 has a pH of 7.1 to 11.5, preferably a pH of 8.5 to 11, in particular a pH of 10 to 11. Accordingly, in a preferred embodiment, the first buffer B1 and/or the second buffer B2 are basic buffers having a pH of 7.1 to 11.5, preferably a pH of 8.5 to 11, in particular a pH of 10 to 11. The pH of the buffers B1 and B2 may be the same of different. Preferably, the difference in pH of buffers B1 and B2 may be less that $\Delta pH$ 2, more preferably less that $\Delta pH$ 1, even more preferably less that $\Delta pH$ 0.5, in particular not more than $\Delta pH$ 0.3 or (essentially) equal. This step is preferably also beneficial in order to elute a (highly purified) Glu-plasminogen product and to achieve a yield >80%.

Thus, in a preferred embodiment, method achieved a yield of Glu-plasminogen of >80%, preferably >85%, in particular >90%, of the initial amount of Glu-plasminogen in the blood plasma or plasma fraction.

Preferably but not necessarily, the composition of the buffers B1 and B2 is (except the presence of cations competing with the cationic groups of the resin of the anion exchanger) (essentially) identical in both buffers. Preferably, buffer B1 comprises between 0.01 and 0.1 M (preferably 0.03 and 0.07 M, in particular 0.05 M) sodium acetate. Exemplarily, the buffer B1 may comprise between 0.01 and 0.1 M (preferably 0.03 and 0.07 M, in particular 0.05 M) sodium acetate and between 0.01 and 0.1 M (preferably 0.03 and 0.07 M, in particular 0.05 M) glycine and may be adjusted to a pH in the range of 8.5 to 11 (preferably a pH in the range of 10 to 11, in particular pH 10.3).

Preferably, buffer B2 comprises between 0.01 and 0.1 M (preferably 0.03 and 0.07 M, in particular 0.05 M) sodium acetate. Exemplarily, the buffer B2 may comprise between 0.01 and 0.1 M (preferably 0.03 and 0.07 M, in particular 0.05 M) sodium acetate and between 0.01 and 0.1 M (preferably 0.03 and 0.07 M, in particular 0.05 M) glycine and between 0.01 and 0.05 M (preferably 0.02 and 0.03 M, in particular 0.025 M) lysine and may be adjusted to a pH in the range of 8.5 to 11 (preferably a pH in the range of 10 to 11, in particular pH 10.5).

As mentioned before, the second buffer B2 comprises a cation competing with the cationic groups of the anion exchanger (competitor cation CC). This may, in principle, be any cation that enables competition with the cationic moieties of the resin of the anion exchanger for the ionic interactions with the Glu-plasminogen.

In a preferred embodiment, in order to enable a particularly beneficial competition with the resin of the anion exchanger, the competitor cation CC used in buffer B2 bears similar chemical and physicochemical properties like the resin of the anion exchanger. Therefore, the person skilled in the art will preferably adapt the competitor cation CC used in buffer B2 to the resin used.

Accordingly, in the view of the above, in a preferred embodiment, the second buffer B2 comprises, as a cation competing with the cationic groups of the anion exchanger, a soluble amine or a salt thereof, preferably a primary $C_1$-$C_{10}$-amine or a salt thereof, in particular lysine or a salt thereof. The concentration of the cation (cationic competitor such as, e.g., lysine or a salt thereof) may be adapted to the educts of the method.

In a preferred embodiment, the concentration of the cation ((cationic competitor such as, e.g., lysine or a salt thereof) is in the range of from 0.001 mol/L to 1.0 mol/L, preferably in the range of from 0.01 mol/L to 0.1 mol/L, more preferably in the range of from 0.01 mol/L to 0.15 mol/L, even more preferably in the range of from 0.01 mol/L to 0.05 mol/L, even more preferably in the range of from 0.02 mol/L to 0.04 mol/L, in particular (approximately) 0.025 mol/L (i.e., 25 mmol/L).

The step of adjusting the pH of the solution obtained from step (iv) to a pH in a desired range (e.g., of from 7 to 8) (step (v)) may be conducted by any means. Optionally, the pH is adjusted by addition of citric acid. Exemplarily, a pH of 7.5 may be obtained. Alternatively, the pH may be adapted from 5.0 to 6.0 or of from 6.0 to 7.5 by addition of acidic acid.

The stabilizers of step (vi) may be any chemical entities that prevent the Glu-plasminogen from maturing into plasmin or Lys-plasminogen. Preferably, a stabilizer (immediately) captures the transformed plasmin molecules to avoid that these molecules activate further plasminogen molecules. Preferably, a stabilizer does not have a negative effect in the human body after parenteral administration of the Glu-plasminogen product. In particular, a stabilizer is not toxic and, particularly preferably, pharmaceutically acceptable.

In a preferred embodiment, the stabilizers of step (vi) are natural stabilizers. Accordingly, a stabilizer is not of synthetic origin. In particular, all stabilizers known in the art to stabilize Glu-plasminogen are suitable in the context of the present invention.

In a preferred embodiment, the stabilizers of step (vi) are selected from the group consisting of aprotinin, alpha-2-antiplasmin (A2AP), D-phenylalanyl-L-prolyl-arginine chloromethyl ketone, small molecule stabilizers, and combinations thereof. In a more preferred embodiment, the stabilizers of step (vi) are selected from the group consisting of aprotinin, alpha-2-antiplasmin, D-phenylalanyl-L-prolyl-arginine chloromethyl ketone, and combinations thereof. Alternatively or additionally, also serpins, glycerol, and/or one or more carbohydrates or derivatives thereof may be used as stabilizers. A carbohydrate may, for instance, be selected from the group consisting of monosaccharides (e.g., glucose, fructose, fucose, xylose, arabinose, mannose, galactose, sorbose), disaccharides (e.g., sucrose, maltose, cellobiose, lactose, xylobiose, turanose, trehalose, melibiose), trisaccharides (e.g., melezitose, raffinose), and oligo- and polysaccharides (e.g., dextran, starch, cellulose, agarose). The used carbohydrates may also be selected and used as described for the stabilization of lipovitelllin III in Hawke and Lea (Biochem. J. 1953 June; 54(3):475-9) and for the stabilization of organisms in Zimmermann (J. Bacteriol., 1962, 84:1297-1302) upon freeze-drying. A carbohydrate derivative may, for instance, be an acylated (e.g., acetylated, methylated) or sulfated form thereof such as, e.g., hydroxypropyl methylcellulose (HPMC, hypromellose), hydroxymethyl cellulose, hydroxyethyl cellulose, hydroxymethyl starch, hydroxyethyl starch, or a combination of two or more thereof.

Any concentration of stabilizers may be used. This concentration should be suitable to avoid maturing into plasmin or Lys-plasminogen.

For example, (optionally recombinant) aprotinin may be used in a concentration range of from 0.1 to 50 µg/mL, in particular in a concentration range of from 0.5 to 35 µg/mL.

For example, (optionally recombinant) aprotinin may be used in a concentration of 30 µg/mL, 6 µg/mL, 2 µg/mL or 0.6 µg/mL. Preferably, (optionally recombinant) aprotinin may be used in a concentration range of from 1 ng to 1 µg per µg of Glu-plasminogen, more preferably of from 10 ng to 0.75 µg per µg of Glu-plasminogen, in particular of from 0.016 µg to 0.48 µg per µg of Glu-plasminogen.

For example, human albumin may be used in a concentration range of from 0.1 µg/mL to 100 mg/mL, preferably in a concentration range of from 1 µg/mL to 50 mg/mL, more preferably in a concentration range of from 5 µg/mL to 20 mg/mL, in particular 0.01-10 mg/mL. Preferably, albumin may be used in a concentration range of from 1 ng to 1 µg per µg of Glu-plasminogen, more preferably of from 10 ng to 25 µg per µg of Glu-plasminogen, in particular of from 0.2 µg to 15 µg per µg of Glu-plasminogen.

The pH and the buffer composition may influence a stable intermediate Glu-plasminogen product.

In a preferred embodiment, in an additional step, the Glu-plasminogen product may be diafiltrated into a further buffer. Preferably, this further buffer may be selected from the group consisting of a phosphate buffer, a citrate buffer, a glycine buffer, and a combination of two or more thereof. More preferably, this further buffer may be selected from the group consisting of a 0.005-0.1 M phosphate buffer of pH 6.6-8.0, a 0.005-0.1 M citrate buffer of pH 7.0-7.4, and a 0.01-0.1 M glycine buffer of pH 4.5-5.5, and a combination of two or more thereof.

The purification method of the present invention leads surprisingly to a Glu-plasminogen product with higher stability in comparison to other purification methods.

As laid out above, the solution obtained from any of steps (iv) to (vi) may be subjected to antiviral treatment. This may improve usability of the purified Glu-plasminogen in a medicinal context because viral contaminations are a concern in products obtained from blood. This may be any antiviral treatment known in the art.

In a preferred embodiment, the solution obtained from any of steps (iv) to (vi) is subjected to antiviral treatment of step (vii), wherein the antiviral treatment selected from the group consisting of:

(vii-a) adding one or more detergents, preferably one or more detergents selected from the group consisting of Tween-20, Tween-80 and Triton-X-100;

(vii-b) adding one or more other antiviral agents such as a phosphate ester, in particular tri-n-butyl-phosphate (TnBP);

(vii-c) ultrafiltration, in particular nanofiltration;

(vii-d) combinations of two or more of the aforementioned; and

After adding one or more detergents (also: solvent detergents (SD)) (step viii-a), such detergents are preferably removed, for example by means of a specific SD-removal resin and/or by means of an anion exchanger. Preferably, a method for removing detergents has (essentially) no influence on Glu-plasminogen and does not introduce any modification on Glu-plasminogen. Preferably, detergents are (essentially) removed (e.g., captured) before a second step of removal of viruses is performed.

Exemplarily, 0.1 to 5% (w/v), preferably 0.5 to 1.5% (w/v), in particular 1% (w/v), Tween-20 may be used. Exemplarily, 0.1 to 0.5% (w/v), preferably 0.2 to 0.4% (w/v), in particular 0.3% (w/v), TnBP may be used. Exemplarily, a combination of 0.1 to 5% (w/v) Tween-20 and 0.1 to 0.5% (w/v), TnBP may be used. In particular, a combination of 1% (w/v) Tween-20 and 0.3% (w/v), TnBP may be used.

Additionally or alternatively to any of the antiviral treatments above, the solution obtained from any of steps (iv) to (vii) or a solid form obtained from step (viii) may be irradiated by UV light and thereby (essentially) sterilized. In a preferred embodiment, a nanofiltration method is used for an additional antiviral removal step.

In a highly preferred embodiment, the method comprises the following steps:
(i) providing blood plasma or a plasma fraction comprising Glu-plasminogen;
(ii) contacting the blood plasma or a plasma fraction with an anion exchanger based on a resin bearing the structure moiety —R—$NH_2$ or —R—$NH_3^+$+$A^-$, wherein R is a $C_1$-$C_{10}$-alkylene residue and $A-$ is an anionic counterion, in particular a lysyl residue;
(iii) washing the anion exchanger obtained from step (ii) loaded with the blood plasma or a plasma fraction with a first buffer B1 having a pH of 8.5 to 11 not comprising cations competing with the cationic groups of the resin of the anion exchanger;
(iv) eluting the Glu-plasminogen from the washed anion exchanger of step (iii) with a second buffer B2 a pH of 8.5 to 11 comprising a primary $C_1$-$C_{10}$-amine or a salt thereof, in particular lysine or a salt thereof, competing with the amino groups of the anion exchanger, thereby obtaining a solution comprising Glu-plasminogen;
(v) adjusting the pH of the solution obtained from step (iv) to a desired pH range (e.g., a pH in the range of from 7 to 8 or of from 4.5 to 5.5, in particular in the range of from 7 to 8);
(vi) stabilizing the Glu-plasminogen by adding one or more stabilizers preventing the Glu-plasminogen from maturing into plasmin or Lys-plasminogen to the solution obtained from any of steps (iv), (v) or (vii), in particular wherein said stabilizers are selected from the group consisting of aprotinin, alpha-2-antiplasmin, D-phenylalanyl-L-prolyl-arginine chloromethyl ketone, small molecule stabilizers, and combinations thereof; and
(vii) subjecting the solution from any of steps (iv) to (vi) to antiviral treatment, in particular wherein said antiviral treatment is:
  (vii-I) adding one or more detergents, preferably one or more detergents selected from the group consisting of Tween-20, Tween-80 and Triton-X-100, and one or more other antiviral agents such as a phosphate ester, in particular tri-n-butyl-phosphate;
  (vii-II) removing the solution of step (vii-I), and thereby removing the one or more detergents (also: solvent detergents (SD)); and
  (vii-III) ultrafiltrating, in particular nanofiltration; and
(viii) optionally drying or freeze drying the solutions comprising Glu-plasminogen obtained from any of steps (iv) or (vii), in particular freeze drying.

Preferably, the buffers B1 and B2 are defined as above and in the example section and in the example section, in particular with respect to their concentration and/or their conductivity.

Further, the contents of the one or more stabilizers and the concentration of the buffers may be used as described above and in the example section.

Optionally, the steps (ii)-(iv) can be repeated with any of the solutions obtained from any of steps (v)-(vii). Herein, the same conditions as laid out above, or other conditions may be used. Also all other steps may be repeated. This may exemplarily be conducted as follows:

In a particularly preferred embodiment, the method comprises the following steps:
(i) providing blood plasma or a plasma fraction comprising Glu-plasminogen;
(ii) contacting the blood plasma or a plasma fraction with an anion exchanger based on a resin bearing the structure moiety —R—$NH_2$ or —R—$NH_3^+$+$A^-$, wherein R is a $C_1$-$C_{10}$-alkylene residue and $A-$ is an anionic counterion, in particular a lysyl residue;
(iii) washing the anion exchanger obtained from step (ii) loaded with the blood plasma or a plasma fraction with a first buffer B1 having a pH of 8.5 to 11 not comprising cations competing with the cationic groups of the resin of the anion exchanger;
(iv) eluting the Glu-plasminogen from the washed anion exchanger of step (iii) with a second buffer B2 a pH of 8.5 to 11 comprising a primary $C_1$-$C_{10}$-amine or a salt thereof, in particular lysine or a salt thereof, competing with the amino groups of the anion exchanger, thereby obtaining a solution comprising Glu-plasminogen;
(v) adjusting the pH of the solution obtained from step (iv) to a pH in a desired range;
(vi) stabilizing the Glu-plasminogen by adding one or more stabilizers preventing the Glu-plasminogen from maturing into plasmin or Lys-plasminogen to the solution obtained from any of steps (iv), (v) or (vii), in particular wherein said stabilizers are selected from the group consisting of aprotinin, alpha-2-antiplasmin, D-phenylalanyl-L-prolyl-arginine chloromethyl ketone, small molecule stabilizers, and combinations thereof; and
(vii) subjecting the solution of step (vi) to antiviral treatment, in particular wherein said antiviral treatment is:
  (vii-I) adding one or more detergents, preferably one or more detergents selected from the group consisting of Tween-20, Tween-80 and Triton-X-100, and one or more other antiviral agents such as a phosphate ester, in particular tri-n-butyl-phosphate; and
  (vii-II) removing the solution of step (vii-I); and
(ii*) contacting the solution obtained from step (vii) with an anion exchanger based on a resin bearing the structure moiety —R—$NH_2$ or —R—$NH_3^+$+$A^-$, wherein R is a $C_1$-$C_{10}$-alkylene residue and $A-$ is an anionic counterion, in particular a lysyl residue;
(iii*) washing the anion exchanger obtained from step (ii*) loaded with the blood plasma or a plasma fraction with a first buffer B1 having a pH of 8.5 to 11 not comprising cations competing with the cationic groups of the resin of the anion exchanger;
(iv*) eluting the Glu-plasminogen from the washed anion exchanger of step (iii*) with a second buffer B2 a pH of 8.5 to 11 comprising a primary $C_1$-$C_{10}$-amine or a salt thereof, in particular lysine or a salt thereof, competing with the amino groups of the anion exchanger, thereby obtaining a solution comprising Glu-plasminogen;

(vii*) subjecting the solution from any of step (iv) to (vi) to antiviral treatment, in particular wherein said antiviral treatment is:
(vii-III*) ultrafiltrating, in particular nanofiltration; and
(v*) optionally adjusting the pH of the solution obtained from step (vii*) to a desired pH range (e.g., a pH in the range of from 7 to 8 or of from 4.5 to 5.5, in particular in the range of from 7 to 8);
(vi*) optionally stabilizing the Glu-plasminogen by adding one or more stabilizers preventing the Glu-plasminogen from maturing into plasmin or Lys-plasminogen to the solution obtained from step (v*), in particular wherein said stabilizers are selected from the group consisting of aprotinin, alpha-2-antiplasmin, D-phenylalanyl-L-prolyl-arginine chloromethyl ketone, small molecule stabilizers, and combinations thereof; and
(viii) optionally drying or freeze drying the solutions comprising Glu-plasminogen obtained from any of steps (vii*), (v*) or (vi*), in particular freeze drying.

Preferably, the buffers B1 and B2, at each occurrence, are defined as above, in particular with respect to their concentration and/or their conductivity.

In a particularly preferred embodiment, the method of the present invention comprises the following steps:
(i) plasma fraction comprising Glu-plasminogen which is selected from the group consisting of:
  (a) cryo-poor plasma, typically obtained from the supernatant of blood plasma subjected to being frozen and subsequently thaw; and
  (b) a waste fraction of paste I+II+III (also I–III) or I+III of the Cohn or Kistler-Nitschmann process or a combination of two or all three of these fractions,
  in particular a waste fraction of paste I+III or paste I+II+III of the Cohn or Kistler-Nitschmann process;
(ii) contacting the blood plasma or a plasma fraction with an anion exchanger based on a resin bearing the structure moiety —R—$NH_2$ or —R—$NH_3^+$+A$^-$, wherein R is a $C_1$-$C_{10}$-alkylene residue and A– is an anionic counterion, in particular a lysyl residue;
(iii) washing the anion exchanger obtained from step (ii) loaded with the blood plasma or a plasma fraction with a first buffer B1 having a pH of 8.5 to 11 in a concentration of from 0.01 to 0.1 M, wherein said first buffer B1 does not comprise cations competing with the cationic groups of the resin of the anion exchanger;
(iv) eluating the Glu-plasminogen from the washed anion exchanger of step (iii) with a second buffer B2 a pH of 8.5 to 11 in a concentration of from 0.01 to 0.1 M, wherein said second buffer B2 comprises a primary $C_1$-$C_{10}$-amine or a salt thereof, in particular lysine or a salt thereof, competing with the amino groups of the anion exchanger, thereby obtaining a solution comprising Glu-plasminogen;
(v) adjusting the pH of the solution obtained from step (iv) to a pH in a desired range;
(vi) stabilizing the Glu-plasminogen by adding one or more stabilizers preventing the Glu-plasminogen from maturing into plasmin or Lys-plasminogen to the solution obtained from any of steps (iv), (v) or (vii), in particular wherein said stabilizers are selected from the group consisting of aprotinin, alpha-2-antiplasmin, D-phenylalanyl-L-prolyl-arginine chloromethyl ketone, small molecule stabilizers, and combinations thereof; and
(vii) optionally subjecting the solution of step (vi) to antiviral treatment.

In a preferred embodiment, the anion exchanger may be regenerated after conducting step (iv) of eluating the Glu-plasminogen. This may be achieved by contacting the anion exchanger with a NaOH or KOH containing aqueous solution. Exemplarily, NaOH in the range of 0.2 to 1.5 M NaOH, more preferably 0.5 to 1 M NaOH may be used for this purpose. Most preferably, 0.1 M NaOH and 0.1 M HCl may be used. This may, for instance support for long life of the individual anion exchanger.

It will be understood that the Glu-plasminogen obtainable (and obtained) from the method of the present invention is particularly pure and well usable for several applications, in particular in the context of treating patients.

Accordingly, a further aspect of the present invention relates to Glu-plasminogen obtainable (obtained) from the method of the present invention.

It will be understood that the definitions and/or preferred embodiments provided in the context of the method above mutatis mutandis apply to the Glu-plasminogen according to the present invention.

The purified naturally occurring Protein Glu-PLG has the same physicochemical and biological properties than the plasminogen in the human body. The physicochemical and biological properties in vivo are laid out herein in more detail. The Glu-plasminogen obtainable (obtained) from the method of the present invention may also be prepared and, optionally also stored, in a frozen, deep-frozen or freeze-dried state and may then be stored at any temperature below the freezing point, such as, e.g., at –35°, –80° C. or in liquid nitrogen.

In a preferred embodiment, the Glu-plasminogen according to the present invention is freeze-dried (also designated as lyophilized). A freeze-dried powder may also be stored at ambient temperature.

In a lyophilization step, one or more agents that stabilize and protect the Glu-plasminogen may be present. This may be a stabilizer as described above one or more carbohydrates or derivatives thereof. For example, a carbohydrate or derivative thereof and/or glycerol may be present.

A carbohydrate may, for instance, be selected from the group consisting of monosaccharides (e.g, glucose, fructose, fucose, xylose, arabinose, mannose, galactose, sorbose), disaccharides (e.g., sucrose, maltose, cellobiose, lactose, xylobiose, turanose, trehalose, melibiose), trisaccharides (e.g., melezitose, raffinose), and oligo- and polysaccharides (e.g., dextran, starch, cellulose, agarose). The used carbohydrates may also be selected and used as described for the stabilization of lipovitelllin III in Hawke and Lea (Biochem. J. 1953 June; 54(3):475-9) and for the stabilization of organisms in Zimmermann (J. Bacteriol., 1962, 84:1297-1302) upon freeze-drying. A carbohydrate derivative may, for instance, be an acylated (e.g., acetylated, methylated) or sulfated form thereof such as, e.g., hydroxypropyl methylcellulose (HPMC, hypromellose), hydroxymethyl cellulose, hydroxyethyl cellulose, hydroxymethyl starch, hydroxyethyl starch, or a combination of two or more thereof As laid out above, the method of the present invention enabled to obtain Glu-plasminogen in extraordinary high purity.

Accordingly, further aspect of the present invention relates to a protein composition comprising at least 80% (w/w), based on the total protein mass, of Glu-plasminogen.

In a preferred embodiment, the protein composition comprises at least 85% (w/w), more preferably at least 90% (w/w) or even at least 95% (w/w), based on the total protein mass, of Glu-plasminogen.

Typically, such protein composition has a particularly high stability and a significantly reduced proteolytic activity, in particular (essentially) no proteolytic activity.

Both glycosylation forms of Glu-plasminogen can be identified in such highly purified protein composition. Preferably, the main impurity is albumin. More preferably, albumin is (essentially) the sole impurity. As mentioned above, albumin may have a stabilizing effect on Glu-plasminogen. Therefore, minor amounts of albumin may optionally be intentionally present in a protein composition. This is described in more detail above, including preferred concentrations thereof.

In a preferred embodiment, the Glu-plasminogen comprised in this composition is obtained from a method of the present invention.

The protein composition may be a solution, a suspension, an emulsion or a dried form as laid out in the context of the method and Glu-plasminogen above. In particular, the protein composition is a freeze-dried powder As laid out above, the protein composition, in particular when it is a freeze-dried powder or a solution, may optionally comprise one or more stabilizing agents such as, e.g., one or more sugars and/or a stabilizer as described above. Content ranges are provided above.

The person skilled in the art knows that such proteins are typically not administered as pure dried proteins, but in a pharmaceutical composition.

Accordingly, in a further aspect, the present invention also relates to a pharmaceutical composition comprising Glu-plasminogen and at least one pharmaceutically acceptable carrier.

It will be understood that the definitions and/or preferred embodiments provided in the context of the method or the Glu-plasminogen above mutatis mutandis apply to the pharmaceutical composition according to the present invention. The terms "pharmaceutical composition" and "pharmaceutical formulation" may be understood interchangeably.

In a preferred embodiment, the Glu-plasminogen comprised in the pharmaceutical composition of the present invention is Glu-plasminogen obtained by a method of the present invention.

As used herein, the terms "pharmaceutically acceptable carrier", "pharmaceutically acceptable excipient", "carrier" and "excipient" may be understood interchangeably in the broadest sense as any substance that may support the pharmacological acceptance of the Glu-plasminogen.

Preferred pharmaceutical compositions enable routes of administration which circumvent the first pass effect. More preferably, the pharmaceutical composition is prepared to be suitable for administration by injection into the patient (e.g., suitable for administration routes selected from the group consisting of intravenous (i.v.), intraarterial (i.a.), intraperitoneal (i.p.), intramuscular (i.m.), and subcutaneous (s.c.) injection). Alternatively or additionally, the pharmaceutical composition may also be suitable for other routes of administration such as, e.g., nasal or transdermal administration.

The pharmaceutical composition ready to use preferably is a liquid formulation, in particular an injection portion. The storage form may also be liquid, but may also be a dried form (e.g. a powder such as a powder comprising dried or freeze-dried Glu-plasminogen) or may be a paste or syrup or the like. Optionally, a dried form, paste or syrup may be dissolved or emulsified prior to being administered to the patient.

A pharmaceutically acceptable carrier may exemplarily be selected from the list consisting of an aqueous buffer, saline, water, dimethyl sulfoxide (DMSO), ethanol, vegetable oil, paraffin oil or combinations of two or more thereof. Furthermore, the pharmaceutically acceptable carrier may optionally contain one or more detergent(s), one or more foaming agent(s) (e.g., sodium lauryl sulfate (SLS), sodium doceyl sulfate (SDS)), one or more coloring agent(s) (e.g., food coloring), one or more vitamin(s), one or more salt(s) (e.g., sodium, potassium, calcium, zinc salts), one or more humectant(s) (e.g., sorbitol, glycerol, mannitol, propylenglycol, polydextrose), one or more enzyme(s), one or more preserving agent(s) (e.g., benzoic acid, methylparabene, one or more antioxidant(s), one or more herbal and plant extract(s), one or more stabilizing agent(s), one or more chelating agents (e.g., ethylenediaminetetraacetic acid (EDTA), and/or one or more uptake mediator(s) (e.g., polyethylene imine (PEI), a cell-penetrating peptide (CPP), a protein transduction domain (PTD), an antimicrobial peptide, etc.).

The present invention also relates to a dosage unit of the pharmaceutical composition of the present invention. Exemplarily, the present invention may refer to a single dose container or to a multiple dosage form.

As indicated above, the Glu-plasminogen, in particular comprised in a pharmaceutical composition, may be very well used in a pharmaceutical context.

Accordingly, in a further aspect, the present invention also relates to Glu-plasminogen for use in a method for treating a patient suffering from or being at risk of developing a disorder selected from the group consisting of organ failure, a thrombotic event, arterial obstructive disease, microcirculation, disseminated intravascular coagulation (DIC), and a combination of two or more thereof in particular organ failure.

In a preferred embodiment, the disorder is organ failure or a thrombotic event.

Plasminogen may be used as a direct treatment opportunity. The currently used tPA (tissue plasminogen activator or uPA (Urokinase)) is used as an indirect therapy requiring at least a normal plasminogen level. tPA may activate the plasminogen to plasmin. This may be used to dissolve an already formed thrombus which may cause consecutive additional tissue damages. The low plasminogen levels in those cases can be caused by the consumption of the Glu-plasminogen protein in-vivo. It was found that the patient often have a low concentration of plasminogen in the plasma during the critical 48 hours. After the injection of Glu-plasminogen, the total level of plasminogen increased over a time period. Additionally, not only the measurement of plasminogen may be decisively but also the amount of alpha-2-antiplasmin. An increased amount of Alpha-2-antiplasmin may inhibit the available plasminogen molecules. Also, in this case, the injection of Glu-plasminogen may balance the high concentration of alpha-2-antiplasmin and may lead to an improvement within the critical 48 hours condition.

Accordingly, in a more preferred aspect, the present invention also relates to Glu-plasminogen for use in a method for treating a patient suffering from or being at risk of developing organ failure.

It will be understood that the definitions and preferred embodiments provided in the context of the method and/or the pharmaceutical composition above mutatis mutandis apply to the Glu-plasminogen for use according to the present invention.

In other words, the present invention also relates to a method for treating a patient suffering from or being at risk of developing a disorder selected from the group consisting of organ failure, a thrombotic event, arterial obstructive disease, microcirculation, disseminated intravascular coagulation (DIC), and a combination of two or more thereof, in particular organ failure, wherein said method comprises administration of Glu-plasminogen to the subject in need thereof.

Organ failure, in particular multi-organ failure, may be caused by a condition selected from the group consisting of infections, sepsis, a (micro-)circulation disorder (e.g., stasis, atherosclerosis, etc.), toxic events, transplantation, an injury, and combinations of two or more thereof. A thrombotic event may be selected from the group consisting of deep vein thrombosis and chronic thromboembolic pulmonary hypertension. Arterial obstructive disease may be associated with or caused by a myocardial, cerebral, kidney, or liver infarction.

In a preferred embodiment, organ failure is failure of an organ selected from the group consisting of the kidney, heart, lung, brain and veins. In a preferred embodiment, organ failure is kidney failure, preferably acute kidney failure (AKI), which is, exemplarily, an acute kidney injury.

Accordingly, in a further aspect, the present invention also relates to Glu-plasminogen for use in a method for treating a patient suffering from or being at risk of developing a disorder selected from the group consisting of organ failure, a thrombotic event, arterial obstructive disease, microcirculation, disseminated intravascular coagulation (DIC), and a combination of two or more thereof, in particular organ failure, said method comprising the administration of Glu-plasminogen for use to said patient.

In a preferred embodiment, the risk of developing a disorder selected from the group consisting of organ failure, a thrombotic event, arterial obstructive disease, microcirculation, disseminated intravascular coagulation (DIC), and a combination of two or more thereof is caused by an inborn or, preferably, an acquired plasminogen deficiency.

Accordingly, in a more preferred embodiment, the risk of developing organ failure or thrombotic event is caused by an acquired plasminogen deficiency. In an alternative preferred embodiment, the risk of developing a disorder selected from the group consisting of organ failure, a thrombotic event, arterial obstructive disease, microcirculation, disseminated intravascular coagulation (DIC), and a combination of two or more thereof is caused by a micro-coagulation disorder.

Accordingly, in a more preferred embodiment, the risk of developing organ failure or thrombotic event is caused by a micro-coagulation disorder.

In a preferred embodiment, the patient is suffering from or is at risk of developing deep vein thrombosis and/or lung embolism.

Accordingly, in preferred embodiment, the present invention also relates to Glu-plasminogen for use in a method for treating a patient suffering from or being at risk of deep vein thrombosis.

Accordingly, in preferred embodiment, the present invention also relates to Glu-plasminogen for use in a method for treating a patient suffering from or being at risk of lung embolism.

In a preferred embodiment, the risk of developing a disorder selected from the group consisting of organ failure, a thrombotic event, arterial obstructive disease, microcirculation, disseminated intravascular coagulation (DIC), and a combination of two or more thereof is caused by an acquired increase of a plasmin inhibitor, in particular wherein the plasmin inhibitor is alpha-2-antiplasmin (A2AP).

Accordingly, in a more preferred embodiment, the risk of developing organ failure or a thrombotic event is caused by an acquired increase of a plasmin inhibitor, in particular wherein the plasmin inhibitor is alpha-2-antiplasmin.

In a preferred embodiment, the disorder is selected from the group consisting of organ failure, deep vein thrombosis, chronic or acute organ embolism, an organ infarction (in particular a heart, kidney, liver, lung, or brain infarction), an acute or chronic inflammation causing a local or generated imbalance of the fibrinolytic system like acute transplant rejection, hypercoagulation, disseminated intravascular coagulation (DIC), and a thrombotic event in an individual organ, in particular wherein the organ is selected from the group consisting of heart, lung and veins.

In a preferred embodiment, the patient is plasminogen deficient. Plasminogen deficiency may be an inborn or acquired plasminogen deficiency.

Plasminogen deficiency may be an acquired plasminogen deficiency and/or displaced coagulation/fibrinolytic balance preferably at micro thrombotic, thrombotic and deep vein a thrombotic event. But also a trauma, huge epithelia disruption or acute or chronic inflammation can result in an acquired plasminogen deficiency and/or displaced coagulation/fibrinolytic balance. Therefore, plasminogen and alpha-2-antiplasmin (A2AP) levels in patients may preferably be measured in an initial blood test, when submitted with organ failure indication. The reduced plasminogen level or an increased ratio of the alpha-2-antiplasmin inhibitor may be used as an indicator for the imbalance of the coagulation and fibrinolytic system. The system is very sensitive due to the administration of Glu-plasminogen, the system can be balanced and a hypercoaguability can be avoided.

As used in the context of the present invention, the term "patient" may be understood in the broadest sense as any living being, which is preferably any animal, more preferably a mammal including human, in particular a human being. It will be understood that the Glu-plasminogen is typically of the same species as the patient to be treated, in order to avoid undesired immunogenic side reactions.

The term "suffering from" as used herein may be understood in the broadest sense in a way that the patient has developed a pathological condition associated with disorder selected from the group consisting of organ failure, a thrombotic event, arterial obstructive disease, microcirculation, disseminated intravascular coagulation (DIC), and a combination of two or more thereof in particular organ failure, i.e., that such disorder is present in the patient. In a preferred embodiment, the term "suffering from" as used herein may be understood in the broadest sense in a way that the patient has developed a pathological condition associated with organ failure, i.e., that organ failure is present in the patient.

The patient suffering from a disorder not necessarily, but optionally bears medicinal symptoms such as, e.g., one or more of the symptoms selected from the group consisting of acid-base disturbances (e.g., respiratory alkalosis or lactic acidosis), oliguria (even anuria), hyperglycemia, increased insulin requirements, tachypnea, hypocapnia, hypoxemia, liver dysfunction, hematologic abnormalities, azotemia, coagulation abnormalities, and ischemic colitis.

The term "being at risk of developing" means that the patient has a certain risk of having a disorder associated with a disorder selected from the group consisting of organ failure, a thrombotic event, arterial obstructive disease, microcirculation, disseminated intravascular coagulation (DIC), and a combination of two or more thereof in particular organ failure. In this context, preferably, the patient has a higher risk compared to the average risk of developing a disorder selected from the group consisting of organ failure, a thrombotic event, arterial obstructive disease, microcirculation, disseminated intravascular coagulation (DIC), and a combination of two or more thereof, in particular organ failure, present in the entire population within the next week (i.e. 7 days). More preferably, the risk is at least 5-fold increased, even more preferably the risk is at least 10-fold increased, even more preferably the risk is at least 100-fold increased, even more preferably the risk is at least 1000-fold increased.

In a preferred embodiment, the present invention relates to Glu-plasminogen for use in a method for treating a patient suffering from a disorder selected from the group consisting of organ failure, a thrombotic event, arterial obstructive disease, microcirculation, disseminated intravascular coagulation (DIC), and a combination of two or more thereof, in particular organ failure.

Preferably, administration is systemic administration (e.g., intravenously (i.v.), intraarterially (i.a.), intraperitoneally (i.p.), intramusculary (i.m.), subcutaneously (s.c.), transdermally, nasally). Alternatively, administration may also be local administration (e.g., intrathecally or intravitreally). Preferably, administration is systemic administration, in particular intravenous injection.

In a highly preferred embodiment, the disorder is selected from the group consisting of organ failure, deep vein thrombosis (DVT). and embolism (e.g., chronic or acute organ embolism). DVT is the formation of a blood clot in a deep vein, most commonly the legs. Complications may include pulmonary embolism, as a result of detachment of a clot which travels to the lungs, and post-thrombotic syndrome. Risk factors include recent surgery, cancer, trauma, lack of movement, obesity, smoking, hormonal birth control, pregnancy and the period following birth, antiphospholipid syndrome, and certain genetic conditions [E. Previtali, P. Bucciarelli, S. M. Passamonti, I. Martinelli, Risk factors for venous and arterial thrombosis, Blood transfusion=Transfusione del sangue, 9 (2011) 120-138; J. Stone, P. Hangge, Deep vein thrombosis: pathogenesis, diagnosis, and medical management, Cardiovascular diagnosis and therapy, 7 (2017) S276-284.]. Genetic factors include deficiencies of antithrombin, protein C, and protein S, and factor V Leiden mutation [J. Stone, P. Hangge, Deep vein thrombosis: pathogenesis, diagnosis, and medical management, Cardiovascular diagnosis and therapy, 7 (2017) S276-s284.]. The underlying mechanism typically involves some combination of decreased blood flow rate, increased tendency to clot, and injury to the blood vessel wall.

Any other states resulting clinically in a hypercoaguability (up to a disseminated intravasal coagulation: DIC) or hypofibrinolytic situation with the formation of thrombi or microthrombi or the delayed clot-dissolving [AA Sharp Thrombus Dissolution J. Clin. Path. 22 (1969) 369.] may be an indication for a plasmin substitution. Also the imbalance in the fibrinolytic system (excess of the inhibitor over the (pro)enzyme plasminogen: ratio larger than 1.25 apha-2-antiplasmin [mg/mL]/plasminogen [mg/mL] may be taken as an indication. Therefore, either a detected inborn or acquired plasminogen deficiency or the detected excess of the inhibitor combined with clinical symptoms suggesting an imminent organ failure for the kidney, lung, heart, brain or the risk for an embolic event or a vein thrombosis may result in the indication of a Glu-plasminogen administration.

There are usually several factors that combine to cause thrombosis. These may be both hereditary and external factors [E. Previtali, P. Bucciarelli, S. M. Passamonti, I. Martinelli, Risk factors for venous and arterial thrombosis, Blood transfusion=Transfusione del sangue, 9 (2011) 120-138; M. A. Islam, S. S. Khandker, F. Alam, M. A. Kamal, S. H. Gan, Genetic risk factors in thrombotic primary antiphospholipid syndrome: A systematic review with bioinformatic analyses, Autoimmunity reviews, (2018)].

Causes of the development of a venous thrombus are according to the still valid Virchowian triad:
1. Change of the blood composition
2. Reduced blood flow rate (stasis).
3. Damage to the inner vessel walls (endothelium)

Risk factors for a thrombosis are oral contraceptives ("pill"), especially in combination with smoking, physical inactivity, especially prolonged lying in the sick, obesity, dehydration (exsiccosis), cancer, past thrombosis, pregnancy. Most commonly affected by deep vein thrombosis are the legs. One then speaks of upper or lower leg vein thrombosis. If both the calf, the popliteal fossa and the thigh are affected, it is called a multi-level thrombosis. A pelvic vein thrombosis is less common, but more dangerous because of the size of the vessel and the higher risk of pulmonary embolism. Pelvic vein thrombosis is feared in pregnant women, where a clot may dissolve after birth due to the lack of compression of the uterus and may lead to pulmonary embolism, which may be fatal. Another complication of thrombosis per se and DVT in particular is disseminated intravascular coagulation (DIC).

It is a classic example of an acquired syndrome with features of intravascular activation of coagulation due to e.g. infectious insults (such as sepsis) and non-infectious insults (such as trauma). The underlying mechanisms of DIC are mediated by inflammatory cytokine-initiated activation of tissue factor-dependent coagulation, insufficient control of anticoagulant pathways and plasminogen activator inhibitor 1-mediated suppression of fibrinolysis. Several clinical complications are associated with DIC such as trauma, liver disease, organ destruction (severe pancreatitis) and malignancies to name a few [S. Gando, M. Levi, C. H. Toh, Disseminated intravascular coagulation, Nature reviews. Disease primers, 2 (2016) 16037].

The administration frequency may be adapted to the individual patient. First, the plasminogen and alpha-2-antiplasmin amount is preferably measured. This may be performed by routine analytic. Administration may be performed once, twice, or more often or continuously (e.g., via drip). Exemplarily, administration may be performed three times daily, twice daily, or every two days or less often.

In a preferred embodiment, the patient is characterized in that:
(a) the ratio of alpha-2-antiplasmin vs. plasminogen (preferably Glu-plasminogen) found in the blood of the patient is at least 1.1fold higher in comparison to the average ratio found throughout population of the same species; and/or
(b) the level plasminogen (preferably Glu-plasminogen) in the blood of the patient is at least 1% (mol/mol) lower in comparison to the average level found throughout population of the same species.

Preferably, the ratio of alpha-2-antiplasmin vs. plasminogen (preferably Glu-plasminogen) found in the blood of the patient is at least 1.15fold higher, more preferably at least 1.2fold higher, in particular at least 1.25fold higher, in comparison to the average ratio found throughout population of the same species. It has been experimentally found that the ratio is on average 1.26fold higher in patients with severe a disorder selected from the group consisting of organ failure, a thrombotic event, arterial obstructive disease, microcirculation, disseminated intravascular coagulation (DIC), and a combination of two or more thereof, in particular organ failure.

Preferably, the level plasminogen (preferably Glu-plasminogen) in the blood of the patient is at least 2% (mol/mol) lower, more preferably at least 5% (mol/mol) lower, in particular at least 10% (mol/mol) lower, in comparison to the average level found throughout population of the same species.

A decreased level of Glu-plasminogen may lead to an imbalance of coagulation and fibrinolysis. The imbalance of the high amount of A2AP and PLG shuts down the fibrinolytic activity and coagulation is not balanced. Especially patients with a disorder selected from the group consisting of organ failure, a thrombotic event, arterial obstructive disease, microcirculation, disseminated intravascular coagulation (DIC), and a combination of two or more thereof, in particular organ failure, were found to show a high ratio of alpha-2-antiplasmin (A2AP) vs. Glu-plasminogen (PLG) in their blood. The application of Glu-plasminogen may therefore be used to "buy time" for the patients (i.e., to stabilize the patient) in combination with current "standard care" treatments. One typical example (for bought time) is maintaining the patent's survival and most important organ functions for at least 48 h, while optionally identifying promising "standard of care" treatments.

Optionally, in particular when the patient shows one or more of the above clinical symptoms, the patient may thus be treated in addition to being administered with the Glu-plasminogen.

Exemplarily, the patient may be subjected to safeguarding hemodynamics and/or artificial respiration. The present treatment may significantly reduce mortality of the patient and allows the improvement of the standard of care.

Current treatment options in the case of acute renal failure are additional treatments with anticoagulants such as heparin. The addition of heparin may lead to inhibition of further coagulation. The humanized plasminogen typically has (essentially) no influence on the coagulation but in the initiation of already build clots. It is known that the binding of heparin may increase the plasmin activity. However, it is assumed that no (significant) pharmacokinetic drug interaction should occur between the treatment with anti-coagulants and with the (human/humanized) Glu-plasminogen of the present invention.

In a preferred embodiment, a patient with multi-organ failure due to sepsis may also be (additionally) treated with means selected from the group consisting of antibiotics and with a thrombosis prophylaxis, organ specific treatment such as dialysis for kidney failure, surgery of multi-organ defects, ventilation therapy and anti-infective therapy for every bacteria, vascular related drugs exhibits systemic vascular effects (catecholamines such as adrenaline or noradrenaline), hemodynamic stabilization, activated protein C (optionally recombinant) and immunoglobulins (e.g., IgG and IgM), and addition of natural protease inhibitors like antithrombin-III (may primary inhibit F.Xa and thrombin).

Organ failure may be understood in the broadest sense as any severe dysfunction of an organ. Preferably, in the sense of the present invention, organ failure is a condition where an organ does not perform its expected function to such degree that normal homeostasis cannot be maintained without external clinical intervention compensating for the dysfunction of the organ.

It has surprisingly found that the administration of Glu-plasminogen (Glu-PLG) could balance the increased amount of A2AP [Seitz, R.; Karges, H. E.; Wolf, M.; Egbring, R. Reduced fibrinolytic capacity and its restoration by plasminogen substitution in acute renal failure. International journal of tissue reactions 1989, S. 39-46]. This was found to enable the reversal of organ failure and reduce the mortality of these patients. Moreover, different diseases are involved in non-reversible blood coagulation as multiple skin necrosis (Waterhouse Friedrichsen Syndrome), further patient with sepsis and hepatitis and cadaver kidney transplantation showed also that the relative concentrations of PLG and A2AP were beneficial for the survival of the transplant.

In a preferred embodiment, the organ failure is or is associated with a pathologic acute renal failure, acute transplant rejection, hypercoagulation, disseminated intravascular coagulation (DIC), and thrombotic event in individual organs, in particular wherein the organ is selected from the group consisting of heart, lung and veins.

In a preferred embodiment, the Glu-plasminogen used in the method for treating a patient suffering from or being at risk of developing organ failure is obtained from a method of the present invention as laid out herein or forms part of a pharmaceutical composition of the present invention.

In a preferred embodiment, the Glu-plasminogen used in the method for treating a patient suffering from or being at risk of developing organ failure is administered in the form of a pharmaceutical composition in the sense of the present invention. Thus, in other words, the present invention also refers to the pharmaceutical composition of the present invention (comprising Glu-plasminogen and at least one pharmaceutically acceptable carrier) for use in a method for treating a patient suffering from or being at risk of developing a disorder selected from the group consisting of organ failure, a thrombotic event, arterial obstructive disease, microcirculation, disseminated intravascular coagulation (DIC), and a combination of two or more thereof, in particular organ failure.

A further treatment step may be conducted. The current treatment option in a hypercoaguability state is the administration of vitamin K antagonists, heparin, or F.Xa inhibitors. This has to be taken as a prophylactic treatment, preventing the formation of new clots and the prolongation of existing clots. The lysis of thrombi can be induced by either tPA (tissue plasminogen activator or uPA (Urokinase)). Both therapies are only in a limited number of patients effective. It seems to be that the patients showing no efficacy suffering from an acquired plasminogen deficiency.

Once this deficiency is detected, the indication for a plasminogen substitution is given [Stoll G.: Molecular mechanisms of thrombus formation in ischemic stroke: novel insights and targets for treatment, Blood 2008, 112: 3555-3562; doi: https://doi.org/10.1182/blood-2008-04-144758]. The same author found in acute thromboembolic stroke the principal treatment goal is to rapidly achieve recanalization of occluded intracerebral vessels. In the case of a permanent vessel occlusion, a complete infarct will inevitably develop. At present, early intravenous or intra-arterial thrombolysis are the only established therapeutic options [The National Institute of Neurological Disorders and Stroke rt-PA Stroke Study Group. Tissue plasminogen activator for acute ischemic stroke. N Engl J Med 1995; 333:1581-1588, Choi J H, Bateman B T, Mangla S, et al. Endovascular recanalization therapy in acute ischemic stroke. Stroke 2006; 37:419-424.] Less than 10% of patients are amenable to this treatment due to the limited time window of up to 3 to 6 hours after symptom onset because of the risk of severe intracerebral hemorrhage with later application [Adams H, Adams R, del Zoppo G, Goldstein L B. Guidelines for the early management of patients with ischemic stroke. Stroke 2005; 36:916-921]. A trial to extend the therapeutic window up to 9 hours by use of recombinant desmoteplase, a novel plasminogen activator, failed [Desmoteplase in Acute Ischemic Stroke-2. [Accessed Feb. 23, 2018]. http://www.strokecenter.org/trials/TrialDetail.aspx?tid=515.]. For unknown reasons, thrombolytic treatment leads to the dissolution of the vessel-occluding clots in some cases, but not in others.

The following examples and claims are intended to provide illustrative embodiments of the present invention described and claimed herein. These examples are not intended to provide any limitation on the scope of the invented subject-matter.

EXAMPLES

Method of Production of Glu-Plasminogen Preparation
Purification Process of Glu-Plasminogen For the isolation of Glu-plasminogen, plasma, cryo-poor plasma, factions from Cohn/Kistler-Nitschmann (KN) process or optional flow through eluate from the 4-PCC (prothrombin complex concentrate) process can be used. A usable process may be summarized as follows:
1. Plasma or cryo-poor plasma
2. optional: capture of 4-PCC complex
3. isolation of Glu-plasminogen and stabilization
4. first virus inactivation (solvent/detergent (SD) treatment)
5. SD removal
6. final purification of Glu-plasminogen complex
7. second virus inactivation (ultra/nanofiltration)
8. formulation (ultrafiltration (nanofiltration), stabilization, freezing, drying)
9. obtaining the Glu-plasminogen product In this process, step 2 can lead to a next generation 4-PCC product. A fraction of step 3 can be introduced into the Cohn/KN (Kistler-Nitschmann) process.

Steps 1-3 can be designated as plasminogen capture step. Steps 4 and 5 can be designated as SD treatment/virus removal. Steps 6 and 7 can be designated as final plasminogen purification.

The process described herein provides (general comments):

Use of modern chromatographic technologies (new resin and bead structure, used in licensed product process already) can handle sanitization standards (1M NaOH) with a maximum of reusability.

Lysine modified gels were used for the isolation process of Glu-plasminogen. But other gels containing free amino groups are usable, too, like other natural or synthetic amino acids, natural and synthetic compounds which containing a free amino group with different spacers.

The process can be integrated in an established fractionation process with minimal regulatory efforts and changes in the cryo-poor plasma stream. The cryo-poor plasma stream was used directly without any changes in the Cohn/KN (Kistler-Nitschmann)-Process for the isolation of IgG, albumin and other proteins.

The capture step achieves higher yields of Glu-plasminogen because of minimized activation of plasminogen due to modern chromatographic steps and resins.

The following Glu-plasminogen yields (step yield/overall yield) were obtained [in % (w/w)]:
1. plasma (100/100)
2. cryo-poor plasma (90/90)
3. isolation of Glu-plasminogen and stabilization (80/72)
4. first virus inactivation (solvent/detergent (SD) treatment) (98/71)
5. SD removal (95/67)
6. final purification of Glu-plasminogen complex (95/64)
7. second virus inactivation (ultra/nanofiltration) (98/62)
8. formulation (ultrafiltration, stabilization, freezing, drying) (90/56)
9. obtaining the Glu-plasminogen product, overall yield: 56% (w/w)

Directly after the isolation, the pH of the Glu-plasminogen was changed with citric acid to pH 7.5 and stabilizer, like aprotinin or alpha-2-antiplasmin (A2AP) were added.

Isolation Process of Glu-Plasminogen from Cryo-Poor Plasma/Plasma Fractions—Process Steps Capture Step: The human plasma or cryo-poor plasma was directly captured on a Lysine Gel (9 CV loadability used). The raw Glu-plasminogen was isolated and stabilized (see example 1.1).

SD-Treatment/$1^{st}$ virus removal: To the raw Glu-plasminogen was added 1% Tween-20 and 0.3% TnBP. The conditions used: 22° C., 2 h and treatment with gentle shaking.

SD-Removal: On a anionic exchanger, Fractogel M TMEA, Merck the SD-solution (diluted 1:10 (10 mM citrate buffer pH 7.6)) was injected (gel: EQ with 25 mM acetate buffer pH 5.75) and all SD-reagents were washed below their specifications). The Glu-plasminogen was eluted with 25 mM acetate buffer pH 5.75 with 0.5 M NaCl).

Final Purification: Same step as Capture Step.

Isolation Process of Glu-Plasminogen—Out of Paste I–III Waste Fractions Obtained from Cohn/KN Process The waste fractions paste I+II+III (i.e., I–III) or paste I+III obtained from Cohn/KN Process can be used for the isolation of Glu-plasminogen.
1. obtaining paste I+II+III (i.e., I–III) or paste I+III from the Cohn/KN (Kistler-Nitschmann) process
2. thawing, dilution, pH adjustment, filtration
3. isolation of Glu-plasminogen
4. stabilization
5. obtaining the Glu-plasminogen product Herein, steps 2-4 can also be considered as referring to the Glu-plasminogen capture step.

Experimental Data
Assay Methods
Detection of Glu-Plasminogen Product

Detection was performed as follows (data not shown): Chromogenic assay detection of plasminogen Siemens Healthcare diagnostic Inc. Newark, Del. 19714 U.S.A, Berichrom Plasminogen.

Detection of Glu-plasminogen-by TECHNOZYMGlu Glu-plasminogen ELISA Kit 96T (Ref: TC12040 Technoclone GmbH, Austria) Technozym: The TC Glu-plasminogen test is a solid phase enzyme immunoassay to determine the amount of Glu- and not Lys-plasminogen. The assay measures Glu-plasminogen in a range from 0.06-0.5 µg/mL. Normal plasma levels are 60-250 µg/mL. The inter- and intra-assay variations are less than 10% and 5%, respectively.

The 96 well plate is precoated with a monoclonal antiplasminogen antibody and blocked with 1% bovine serum albumin (BSA), lyophilized. (TC-Code GX)). The samples and the standard (lyophilized Normal Plasma, (TC-Code BJ)) are diluted with the incubation buffer (PBS; pH 7.3); containing stabilizer protein; 0.05% proclin; and blue dye. The standard curve contains Glu-plasminogen concentrations of 0.5 µg/mL, 0.25 µg/mL, 0.125 µg/mL, 0.063 µg/mL and 0.0 µg/mL.

Pipette 0.1 mL of the diluted samples/standard into separate wells. Running standard/sample in duplicate is recommended. Cover the plate with a plastic foil and incubate overnight at 4° C. 3. Reconstitute (required) strips by adding 0.25 mL of wash buffer (Concentrate—(Predilution 1+11.5) (PBS; pH 7.3) containing detergent; 0.01% merthiolat) to the wells and tip out the contents. Wash the strips four times further with wash buffer. Tap strips on absorbent paper and make sure the wells are completely dry. Add 0.1 mL of the diluted PDX anti-plasminogen antibody to all wells, preferably with a multichannel pipette. Cover and incubate the plate for 1 hour at 37° C. Wash five times as described before. Pipette 0.1 mL of TMB substrate to all wells. Incubate for 15 minutes at room temperature. Pipette 0.1 mL of stop solution to all wells. Measure absorbances at 450 nm (with 620 nm reference filter if available). Read absorbances within one hour after the addition of the stop solution. Construct a graph of standard curve. Locate the absorbance for each sample on the curve and read the corresponding value from the horizontal axis. Do not forget to multiply by the dilution factor for the samples.

SDS-PAGE

To determine the purity of the Glu-plasminogen, SDS-PAGE was used with an additional Coomassie staining. The BioRad Mini-Protean TGX Stain free gels 4-20% (Cat: 456-9093) were used in combination with Precision Plus Protein Standards all blue (BioRad Cat: 161-0373), Glu-plasminogen standard (Coachrom Cat: HPGG) and Lys-plasminogen Standard (Coachrom Cat: HPGL). The proteins were stained with Bio Safe™ Coomassie G-250 Stain (Bio-Rad Cat: 161-0786). The background was destained with destilled $H_2O$.

Bradford Method—Determination of Total Protein

The Quick Start™ Bradford protein assay is a simple and accurate procedure for determining the concentration of protein in solution. The assay supplies ready-to-use dye reagent at 1× concentration (BioRad: Cat #500-0205). Protein concentration is determined in one step. Quick Start Bradford protein assay kits offer bovine serum albumin standard sets (BioRad: Cat #500-0206). From Samples and from the prediluted standard concentrations (0.125, 0.25, 0.5, 0.75, 1.0, 1.5, and 2.0 mg/ml) 5 µL were added into a polypropylen 96 well plate F-bottom (Eppendorf: Lot: G171297G). Finally, 250 µL Dye Reagent is added to each well. Mix wells and incubate the 96-Well Plate at 37° C. for 5 min (max 60 min). The absorption kinetics were measured at 595 nm at 37° C. using a spectrophotometer; locate the absorbance for each sample on the curve and read the corresponding value from the horizontal axis.

Distribution of molecular size analyzed by HPLC Size Exclusion Chromatography (SEC) for Glu-plasminogen product.

The below method can be utilized to determine the percentage of aggregates in Glu-plasminogen preparations (as used in Example 1.4, 1.6).

Test Solution:

Samples were injected undiluted at approx. 1 g/L with an injection volume of 100 µL. As reference solution Glu-plasminogen (e.g. Coachrom HPPG) was used. The standard solution was from Bio-Rad (gel filtration standard, Art.-No. 151-1901)

A Column (size: 1=30 mm, Ø=7.8 mm) was used with the stationary phase from Tosoh Bioscience TSK-Gel G4000 SWXL. As mobile phase, a buffer was generated containing 4.873 g of disodium hydrogen phosphate dihydrate, 1.741 g of sodium dihydrogen phosphate monohydrate, 11.688 g of sodium chloride and 50 mg of sodium azide, dissolved in 1 liter of water. Flow rate was at 0.5 mL/min. The detection was carried outspectrophotometrically at 280 nm. The chromatograms obtained were compared with the reference solution. The chromatogram was integrated according to the following scheme and the peaks were identified:

Polymer (>1200 kD), 10-13 min
Proteins high molecular weight (150-900 kD), 13-22 min
Glu-plasminogen (92 kDa): 22-24 min
Albumin (66 kD), 25-27 min
Fragments (<100 kD), 26-40 min Determination of Proteolytic Activity The proteolytic activity was assessed by mixing a chromogenic substrate (in particular those sensitive to at least one serine protease) and a sample of the Glu-plasminogen preparation (usually diluted in buffer to meet the linear range of the assay) at 37° C. and monitoring the absorption kinetics using a spectrophotometer. The proteolytic activity of the sample is calculated from the initial absorption (extinction E) difference ($\Delta E$/min) by using the equation C (U/L)=S×$\Delta E$/min×F (C=proteolytic activity; S=conversion factor relating to specific adsorption change of the chromogenic substrate; and F=dilution factor). Use of the substrate is according to manufacturer's instructions. The proteolytic activity can in particular be assessed via the following steps:

(a) 25 mg of the substrate S-2288 (Chromogenix) is dissolved in 7.2 mL of water-for-injection;
(b) a sample of the Glu-plasminogen preparation is diluted into buffer (100 mM Tris-HCl pH 8.4, 106 mM NaCl) to meet the linear range of the assay and temperature is adjusted to 37° C.;
(c) equal amounts (e.g. 100 µl) of the diluted Glu-plasminogen preparation and the dissolved substrate were mixed;
(d) the absorption kinetics were measured at 405 nm for 1 to 3 minutes at 37° C. using a spectrophotometer;
(e) the proteolytic activity of the sample is calculated from the initial absorption difference ($\Delta E$/min) by using the equation C (U/L)=313×$\Delta E$/min×F (C=proteolytic activity, F=dilution factor)

The limit of quantitation of this method is 8 U/L, and using a sample of the Glu-plasminogen preparation proteolytic activity is undetectable. As such the level of the proteolytic activity in the final product was found below 8 U/L.

Experimental Example 1—Isolation Process of Glu-Plasminogen

Material and Methods

Chromatography experiments were performed using a 1 cm internal diameter, 5 cm bed height chromatography column (Gotec Labortechnic) together with a Bio-Rad NGC Chromatography system. The column (Lysine Hyper D Resin) was equilibrated with PBS Buffer pH 6.6 (5×) at a contact time of 5 min. Cryo-poor plasma/flow through PCC was then loaded at a contact time of 5 min.

Post-load wash was with 0.05 M Na-acetate/0.05 M glycine buffer pH 10.3 to baseline absorbance.

The column was then eluted with 0.05 M Na-acetate/0.05 M glycine buffer/0.025 M Lysine pH 10.3 at a contact time of 5 min, and regenerated with 0.5 M sodium hydroxide. Load, non-bound, and elution fractions were analyzed by nephelometry to determine IgG and albumin content. SDS PAGE was carried out to determine purity. ELISA was carried out to determine plasminogen content.

Results

Plasminogen was isolated with a yield of 84% (recovery 84%) from the flow through fraction of the 4-PCC product.

| Sample | Plasminogen [IU/dL] | Plasminogen [IU] | Yield [%] |
|---|---|---|---|
| Feed | 84.4 [66 mL] | 55.7 | 100 |
| Flow Through | <17.7 [85 mL] | 15.0 | 0 |
| Capture Fraction | 316.4 [10.0 mL] | 31.6 | 83.6 |

Total Protein

The Total Protein (TP) yield of the flow through fraction was quantitative within the error range. The plasminogen capture fraction shows a TP content of 1.0 g/L, which demonstrates a very pure product. No interaction of albumin, IgG, with the column resulted in a 100% flow through. The eluted Glu-Plasminogen had very low total protein concentration which resulted in a minimized impurity.

| Sample | Total Protein [mg/mL] | TP Absolut [mg] | Yield [%] |
|---|---|---|---|
| Feed | 55.313 [66 mL] | 3651 | 100.0 |
| Flow Through | 43.219 [85 mL] | 3673 | 100.6 |
| Capture Fraction | 1.031 [10.0 mL] | 10.3 | 0.28 |

Albumin

The albumin content in the flow through fraction was 104% (quantitative, within error ranges).

| Sample | Albumin [mg/mL] | Albumin Absolut [mg] | Yield [%] |
|---|---|---|---|
| Feed | 31.971 [66 mL] | 2110.1 | 100.0 |
| Flow Through | 25.800 [85 mL] | 2193.0 | 104.0 |
| Capture Fraction | — [10.0 mL] | — | — |

IgG

The IgG content in the flow through fraction was 99.5% (quantitative, within error ranges).

| Sample | IgG [mg/mL] | IgG Absolut [mg] | Yield [%] |
|---|---|---|---|
| Feed | 8.79 [66 mL] | 580.14 | 100.0 |
| Flow Through | 6.79 [85 mL] | 577.15 | 99.5 |
| Capture Fraction | — [10.0 mL] | — | — |

Experimental Example 1.1—Isolation Process of Glu-Plasminogen from Cryo-Poor Plasma Glu-Plasminogen can be purified from cryopoor plasma with the method mentioned in example 1. As contact time 10 min was used. The load ability of cryo-poor plasma was 8 CV (40 mL cryo-poor plasma). The eluted Glu-Plasminogen gained comparable yields as in example 1. The yield was 76% with a recovery of Glu-Plasminogen of 85%.

Product Specification and Administration of Glu-Plasminogen

The purified naturally occurring protein Glu-plasminogen will be used for multiple occasions on several days.

Target purity of the plasminogen preparation is ≥90%, containing at best exclusively Glu-plasminogen and not Lys-plasminogen. Activation of inactivated Glu-plasminogen molecules can be initiated by Lys-plasminogen. Lys-plasminogen was already enzymatically cleaved and has an open conformation for a faster activation process to plasmin. Therefore, Lys-plasminogen is not usable for the application into a human body because of the unspecific activation, followed by strong adverse effects. The usage of modern technology of chromatographic resins and SD-treatment resulted in minimal losses of plasminogen during the total process and high yields of inactivated Glu-plasminogen. Potential activation from Glu- to Lys-plasminogen was balanced by Aprotinin, which captured the activation process (Lys-plasminogen and Plasmin). Additionally, several inhibitors such as the natural inhibitor A2AP and pPack were tested for stabilizing the inactivated Glu-plasminogen product.

Experimental Example 2—Comparison of Buffers and Resins for Capture-Step-Of Glu-Plasminogen from PCC Flow Through Studies were performed to determine efficacy of two different resins for a first Glu-plasminogen capture step. The Resin Lysine Hyper D (Pall) and the ECH-Lysine Sepharose™ 4 Fast Flow (GE Healthcare) were analyzed. The Glu-plasminogen was purified from the feed stream flow through Pro Thrombin Complex (PCC). This feed contains IgM 0.8 g/L, IgG 8.83 g/L, albumin 32.49 g/L, total protein (TP) 57 g/L and Glu-plasminogen 74 µg/mL. The column chromatography was performed with a öeGötec column (d 1 cm h: 20 cm) using a Biorad NGC Chromatography System.

A column was used with a column volume (CV) of 4-5 mL. A constant contact time of 7- or 8 min was applied in each experimental approach. The feed passed the column with a flow rate of 0.5-0.6 mL/min. The feed loadability was constant at 10 CV.

The column was equilibrated (4 CV) with 0.05 M phosphate buffer pH 6.6 (Method 1) or with 0.01 M Tri-Na-citrate/1 mM $CaCl_2$/0.12 M NaCl pH 7.0 (Method 2) or 0.1 M phosphate buffer pH 7.4 (Method 3). The pure flow through PCC (pH 7.3 13.5 mS/cm) passed the column. As a wash buffer 0.05 M acetate/0.05 M glycine pH10.3 (Method 1) or with 0.01 M Tri-Na-citrate/1 mM $CaCl_2$/0.12 M NaCl pH 7.0 (Method 2) or 0.1 M phosphate buffer pH 7.4 (Method 3) was used. The flow though was collected in bottles and frozen at −35° C. For elution of Glu-plasminogen either 0.05 M acetate/0.05 M glycine/0.025 M Lysine pH 10.3 (Method 1), 0.05 M Tris/0.025M Lysine/1 M NaCl pH 9.0 (Method 2) or 0.1 M phosphate buffer 0.2 M ε-aminocaproic pH 7.4 (Method 3) as was used. As cleaning in place (CIP) program 0.1 M NaOH (4 CV), 0.1 M HCl (4CV) was used and the column was stored in 20% ethanol. The final Glu-plasminogen product was frozen at −35° C. A Glu-plasminogen ELISA Technozym was used to determine Glu-plasminogen concentration. The immunoglobulin concentration was analyzed nephelometrically. The albumin concentration was determined by polychromatic endpoint determination and TP by Bradford method.

The results indicate, that the usage of different resins and different buffer conditions leads to variable results. The aim is to first bind Glu-plasminogen and then elute Glu-plasminogen with a high yield. The other proteins should flow through with 100%. This flow through is mostly used for further purification in in other processes. The results indicate that IgG and albumin flow through with 100% by the usage of both resins. The IgM molecules interact with the column depending on different buffer conditions. The best flow through result could be achieved by the usage of the method 1 with both resins (Table 1).

TABLE 1

Glu-plasminogen purification on two different resins using Method 1, 2 and 3, Analysis of fflow-through.

| | | | Flow-through | | | |
|---|---|---|---|---|---|---|
| Method | Resin used | 10 CV-Volume-FT [mL] | total IgM recovery | total IgG recovery | total Albumin recovery | total Protein recovery |
| 1 | Lysine Hyper-D | 57.3 | 103% | 110% | 108% | 106% |
|   | Lysine-Sepharose- | 63.6 | 104% | 102% | 98% | 103% |
| 2 | Lysine Hyper-D | 59.9 | 74% | 90% | 102% | 103% |
|   | Lysine-Sepharose- | 65.4 | 96% | 98% | 99% | 102% |
| 3 | Lysine Hyper-D- | 58.5 | 90% | 103% | 104% | 100% |
|   | Lysine-Sepharose- | 65.9 | 85% | 98% | 108% | 103% |

* ±10% Inter- and 5% intra-assay variations.

The yield of Glu-plasminogen varies with the usage of the resin Lysine Hyper D in combination with the three methods. The highest yield of Glu-plasminogen can be achieved by method 1. The plasminogen yield is 90% and respectively the recovery (Glu-Plasminogen yield+Glu-Plasminogen in flowthrough) at around 95%. The intended application of the resin ECH-Lysine Sepharose results in comparable Glu-plasminogen yields for each of the three methods.

The usage of method 1 with the Lysine Hyper D and Lysine Sepharose Resins resulted in higher purities of the Glu-plasminogen preparation in comparison to the other methods 2 and 3.

TABLE 2

Glu-plasminogen purification on two different resins using Method 1, 2 and 3, Analysis of eluates.

| | | | Eluate | | Plasminogen |
|---|---|---|---|---|---|
| Method | Resin used | Volume-Eluate [mL] | Glu-plasminogen [µg/mL] | Plasminogen yield (Eluate) | recovery (E + FT) |
| 1 | Lysine Hyper-D- | 5.73 | 527 | 90% | 95% |
|   | Lysine-Sepharose- | 3.99 | 753 | 83% | 83% |
| 2 | Lysine Hyper-D- | 7.33 | 253 | 69% | 77% |
|   | Lysine-Sepharose- | 6.86 | 519 | 81% | 81% |
| 3 | Lysine Hyper-D- | 4.07 | 392 | 50% | 65% |
|   | Lysine-Sepharose | 4.29 | 680 | 81% | 81% |

* ±10% Inter- and 5% intra-assay variations

Experimental Example 3—P Purification of Glu-Plasminogen with 10 mM Acetate Buffers and Loadability Up to 25 CV This example was performed to determine the binding capacity the resin ECH-Lysine Sepharose™ 4 Fast Flow (GE Healthcare) in a first Glu-plasminogen Capture Step. The Glu-plasminogen was purified from the feed stream flow through Pro Thrombin Complex (PCC). This feed contains IgM 0.8 g/L, IgG 8.83 g/L, albumin 32.49 g/L, Total protein (TP) 57 g/L and Glu-plasminogen 74 µg/mL. The column chromatography was performed with aGötec column (d 1 cm h: 20 cm) using a Biorad NGC Chromatography System.

A column was used with a column volume (CV) of 5.02 mL and the chromatographic purification was performed with a constant contact time of 7.8 min. The feed passed the column with a flow rate of 0.64 mL/min. The feed loadability was up to 25 CV.

The column was equilibrated (4 CV) with 0.05 M phosphate buffer pH 6.6 (Method 1). The pure flow through PCC (pH 7.3 13.5 mS/cm) passed the column. The 0.01 M acetate/0.05 M glycine pH10. was used as a wash buffer. The flow-through and the wash fraction was collected in bottles and frozen at −35° C. The buffer 0.01 M acetate/0.05 M glycine/0.025 M lysine pH 10.3 was used to eluate Glu-plasminogen. More acidic or neutral pH values resulted in a reduction of Glu-plasminogen yields. For the CIP program 0.1 M NaOH (4 CV), 0.1 M HCl (4 CV) was used and the column was stored in 20% ethanol.

The pH value of eluted Glu-plasminogen product was adjusted with 1M acetic acid to pH 5.0. To produce a stable Glu-plasminogen without additives the product was diafiltrated (Pall 10 kDa Centrifugal device Number MCP010C41) into a 0.32 M glycine buffer and was frozen at −35° C. A Glu-plasminogen ELISA Technozym was used to determine Glu-plasminogen concentration. The immunoglobulin concentration was analyzed nephelometrically. The albumin concentration was determined by polychromatic endpoint determination and TP by Bradford method.

This example demonstrates the advantages to use the ECH-Lysine Sepharose with an 0.01 M acetate buffer for washing and Glu-plasminogen elution. The resin offers a high loadability >25CV of the feed and a high Glu-plasminogen yield of 93% under the mentioned conditions. The ECH-Lysine Sepharose can be used with a high binding capacity of min. 1.85 mg plasminogen/mL Resin. Especially the purity of Glu-plasminogen product is extremely high with >90%. Coomassie-stained SDS-PAGE detects only albumin as an impurity with <10%. However, the presence of albumin offers an additional stabilizing effect (Table 3).

TABLE 3

Step Yields of the Glu-plasminogen purification process with the use of 10 mM acetate buffers andand a loadability up to 25 CV.

| Exp: Number:<br>02_PLG_01_CH_028.2 | Glu-PLG<br>[µg/mL] | IgM<br>[g/L] | IgG<br>[g/L] | Albumin<br>[g/L] | Total protein<br>[g/L] |
|---|---|---|---|---|---|
| Feed (25 CV/125 mL) | — | — | — | — | — |
| volume [L] | | | 0.1256 | | |
| concentration [g/L] | 0.064 | 0.743 | 8.650 | 30.482 | 53.258 |
| total protein [g] | 0.008 | 0.093 | 1.086 | 3.829 | 6.689 |
| Flow Through | — | — | — | — | — |
| volume [L] | | | 0.125 | | |
| concentration [g/L] | | 0.726 | 8.220 | 31.132 | 52.439 |
| total protein [g] | 0 | 0.091 | 1.028 | 3.892 | 6.555 |
| Wash-Fraction | — | — | — | — | — |
| volume [L] | | | 0.01656 | | |
| concentration [g/L] | | <0.053 | 3.180 | 12.234 | 20.354 |
| total protein [g] | 0.00000 | 0.001 | 0.053 | 0.203 | 0.337 |
| Eluate - Glu-plasminogen | — | — | — | — | — |
| volume [L] | | | 0.00547 | | |
| concentration [g/L] | 1.36 | <0.053 | <0.350 | 0.412 | 1.452 |
| total protein [g] | 0.007 | 0.000 | 0.002 | 0.002 | 0.008 |
| Yield-Glu-plasminogen | 93% | 0% | 0% | 0% | 0% |
| Recovery of Plasma proteins | 93% | 98% | 100% | 107% | 103% |

\* ±10% Inter- and 5% intra-assay variations

Experimental Example 4 Capture of Glu-Plasminogen from Fraction I+II+III and Resulting Waste Fractions The fraction I+II+III (140 g) originating from cold ethanol fractionation of human plasma was suspended in 760 mL Buffer (0.1 M acetate buffer pH 5.05). The suspension was mixed for 15-30 minutes after the suspension temperature is reached (22° C.). In the suspension, a Glu-plasminogen concentration of 73 µg/mL was measured. After filtration by depth filtration or centrifugation, Glu-plasminogen might be purified from the resulting filtrate/supernatant according to example 3.

In a second option, the suspension was further treated by addition of octanoic acid (0.110 kg per kg fraction I+II+III used) at room temperature and the protein solution was further mixed for 80 minutes, using a vibrating mixer (Vibromixer®, Size 4) The octanoic acid was added slowly over 30 min. Approx. 0.015× amount of fraction I+II+III of tri-calcium phosphate ($Ca_3PO_4)_2$) was added and the protein solution was further mixed for 15-30 min. Filter aid Celpure® P100 (4.3-5.7 g/kg protein solution) was added into the suspension and incubated for 15 min. Additionally, Filter aid Harbolite® 900 (10 g/kg protein solution) was added into the suspension and incubated for 15 min.

The precipitate was separated from the filtrate by depth filtration. The filtrate contains 80% of IgG, IgM and albumin of the starting suspension, Glu-plasminogen could not be detected. However, proteins remain in the filter cake (wastefraction), which is usually removed and discarded, but seems to have a high potential to regenerate new proteins (Glu-Pasminogen). Isolation of Glu-plasminogen from the precipitate (filter cake) by several washing steps was successful with a concentration of ~28 µg/mL, resulting in a yield of 38% from the starting material. As the filter cake, being a waste fraction, is usually discarded, the yield is subordinate to the fact, that indeed native Glu-plasminogen can be obtained by recycling of waste fractions. Therefore, also other waste fractions of the Cohn/KN process can be used for isolation and further purification of Glu-plasminogen.

The Glu-plasminogen isolated from the filter cake may be further purified: The Glu-plasminogen solution was diluted in 0.05M phosphate buffer at pH 6.6. The final Glu-plasminogen capture step was performed according to example 3.

In general, the Glu-plasminogen can be isolated from each fraction I+II+III and resulted waste fraction. The Glu-plasminogen concentration differs of each individual Cohn or Kistler-Nitschmann process.

Experimental Example 5 Purity of Glu-Plasminogen Preparation

The Glu-plasminogen product was purified by a selective affinity chromatography. Although the Lysine residues have a high affinity, impurities can be captured as well. Furthermore, the purification process of Glu-plasminogen can generate aggregates or fragments. The Glu-plasminogen should have a high purity without presence of aggregates or fragments. In Table 4, SEC analysis of the Glu-plasminogen products purified by Example 2 are shown. The different methods show similar results. Only the Glu-plasminogen product purified by Method 2 with Lysine Hyper D shows molecules with high molecular weight. The other Glu-plasminogen products contain no fragments and no aggregates. The albumin content in the Glu-plasminogen products varies minimally between 10-20%.

TABLE 4

SEC-Analysis of Glu-plasminogen (PLG) product (left column Method No. 1-3)

| | | | SEC-Relative-Area | | | |
|---|---|---|---|---|---|---|
| Resin used | Total Protein Content [µg] | Aggregates >1200 kDa | molecules high molecular weight >630 kDa | PLG (92 kDa) | Albumin (66 kDa) | Fragments <100 kDa |
| 1 Lysine Hyper-D | 46.9 | n.d. | n.d. | 84% | 16% | n.d. |
| Lysine-Sepharose | 37.2 | n.d. | n.d. | 89% | 11% | n.d. |
| 2 Lysine Hyper-D | 25.3 | n.d. | 9% | 81% | 19% | n.d. |
| Lysine-Sepharose | 51.9 | n.d. | n.d. | 88% | 12% | n.d. |
| 3 Lysine Hyper-D | 39.2 | n.d. | n.d. | 81% | 19% | n.d. |
| Lysine-Sepharose | 68.0 | n.d. | n.d. | 87% | 13% | n.d. |
| PLG Standard Coachrom | 104.4 | n.d. | n.d. | 78% | 22% | n.d. |

* ±10% Inter- and 5% intra-assay variations

Experimental Example 6—Determination of Residual Proteolytic Activity of Purified Glu-Plasminogen Products The Glu-plasminogen purification was performed according to example 2. The proteolytic activity in samples of Glu-plasminogen products (e.g. c: 250 µg/mL) purified by the before mentioned purification methods was determined using the chromogenic substrate S-2288 (Chromogenix), following the manufacturer's instructions. 25 mg of the substrate S-2288 (Chromogenix) were dissolved in 7.2 mL water-for-injection. Samples were diluted into buffer (100 mM Tris/HCl pH 8.4, 106 mM NaCl) to meet the linear range of the assay, 100 µL buffer were mixed with 100 µL sample (mixing and temperature adjustment to 37° C.). 100 µL of the prediluted sample were mixed with 100 µL chromogenic substrate solution into a 96-well plate. The absorption kinetics are measured at 405 nm (1-3 min) at 37° C., using a spectrophotometer. The proteolytic activity of the sample was calculated from the initial absorption difference ($\Delta E/min$) by using the equation C (U/L)=313*$\Delta E/min$*F (C=proteolytic activity, F=dilution factor).

TABLE 5

Proteolytic activity of Glu-plasminogen products.

| | Determination of proteolytic activity Starting material (U/L) 30 | |
|---|---|---|
| Mean residual proteolytic activity in Glu-plasminogen Product (U/L) | Lysine Hyper D | Lysine Sepharose |
| Method 1 | 50.6 | <8 |
| Method 2 | 486.8 | <8 |
| Method 3 | 32.5 | <8 |
| Method 1-DF Glycine r | <8 | |

* ±10% Inter- and 5% intra-assay variations

The purified Glu-plasminogen products show different proteolytic activity levels depending on the purification method. In some samples an increased proteolytic activity could be determined due to buffer conditions or resin characteristics. To compare the different purification methods, Glu-plasminogen concentration was similar in each sample. Glu-plasminogen products purified by the usage of ECH-Lysine-Sepharose had no proteolytic activity.

This result indicates, that the purification method does not activate Glu-plasminogen and does not purify other contaminating proteases.

After purification with Lysine Hyper D resin higher proteolytic activities were measured, varying with the use of different buffer conditions. Saturating the Lysine Hyper D column with aprotinin minimizes the proteolytic activity of the generated Glu-plasminogen preparations. Furthermore, proteolytic activity was drastically reduced after diafiltration into 0.32M glycine buffer.

Experimental Example 7—Storage Stability Studies with Liquid Glu-Plasminogen Product Glu-plasminogen products prepared according to examples 2 and 3 were incubated at 37° C. over a time course of 48 h and analyzed afterwards for the presence of degradation products (e.g. Lys-plasminogen) according to SDS-PAGE. Furthermore, the remaining content of Glu-plasminogen after 48 h of incubation was determined by Glu-plasminogen ELISA.

According to Coomassie-stained SDS-PAGEs, the stability of Glu-plasminogen in the preparations depend on the chromatographic resin used for purification as well as on buffers used for elution and storage of Glu-plasminogen. The Glu-plasminogen content of a preparation generated using method 1 on Lysine-sepharose, that was diafiltrated into 0.32 M glycine buffer pH 4.3, stayed constant over a time course of 48 h at 37° C. No degradation to Lys-plasminogen could be detected in the sample. In some of the other Glu-plasminogen products prepared according to example 2, degradation processes of Glu-plasminogen were visible.

This tendency can also be observed by measuring the remaining Glu-plasminogen content after 48 h at 37° C. of the different Glu-plasminogen preparations using a Glu-plasminogen ELISA (table 6). The Glu-plasminogen concentration of each sample at time point t=0 was defined as 100%.

TABLE 6

Stability-study of liquid Glu-plasminogen product.

| | purified Glu-plasminogen content | Storage in hours at 37° C. | | | | | |
|---|---|---|---|---|---|---|---|
| Method | Resin used | 0 | 3 | 7 | 18 | 24 | 48 |
| 1 | Lysine Hyper-D | 100% | 100% | 82% | 4% | 0% | 0% |
| | Lysine Hyper-D-Glycine-Diafiltrated | 100% | 100% | 100% | 100% | 100% | 100% |

TABLE 6-continued

Stability-study of liquid Glu-plasminogen product.

| Method | purified Glu-plasminogen content Resin used | Storage in hours at 37° C. | | | | | |
|---|---|---|---|---|---|---|---|
| | | 0 | 3 | 7 | 18 | 24 | 48 |
| | Lysine-Sepharose | 100% | 100% | 100% | 100% | 100% | 80% |
| | Lysine-Sepharose-Glycine-diafiltrated | 100% | 100% | 100% | 100% | 100% | 100% |
| 2 | Lysine Hyper | 100% | 70% | 5% | 0% | 0% | 0% |
| | Lysine-Sepharose | 100% | 100% | 100% | 92% | 18% | 2% |
| 3 | Lysine Hyper-D | 100% | 100% | 75% | 3% | 0% | 0% |
| | Lysine-Sepharose | 100% | 100% | 100% | 100% | 100% | 70% |

* ±10% Inter- and 5% intra-assay variations

Generally, it can be observed, that Glu-plasminogen products show a higher stability, if purified by ECH-Lysine Sepharose in contrast to Lysine Hyper D. However, independent of the resin used for purification, Glu-plasminogen products eluted with acetate buffer could be further stabilized by diafiltration into glycine buffer, showing similar high stabilities afterwards. The stability analysis indicates, that the usage of buffer conditions from method 1 resulted in a highly stable purified Glu-plasminogen product.

After incubation of this preparation at 37° C. for 48 h, the product remained within the specifications defined to show stability of the Glu-plasminogen preparation: presence of degradation products (e.g. Lys-plasminogen) according to SDS-PAGE, aggregate and fragment content measured with high performance size exclusion chromatography (HPSEC), proteolytic activity (PA) and determination of the remaining content of Glu-plasminogen after 48 h incubation by Glu-plasminogen ELISA (see table 7).

Other parameters like coloration, opalescence, pH value were also determined and stayed unchanged over the whole study period.

In the ongoing stability study, also after 96 h the preparations show the same stability profile, confirming the hypothesis, that the stability of a Glu-plasminogen product depends on buffer compositions, used chromatographic resin, pH value and conductivity.

Additionally, in a second stability study over 48 h at 37° C., it was demonstrated, that addition of rec. aprotinin (0.019 µg rec. aprotinin/µg Glu-plasminogen) further increased stability of Glu-plasminogen products, independent of the storage buffers used.

TABLE 7

Stability study of a liquid Glu-plasminogen product
(Method 1. Lysine-Sepharose_glycine diafiltrated)
with specific product specifications.

| Parameters tested | Requirement (Tolerance) | Storage in hours at 37° C. | | | | | |
|---|---|---|---|---|---|---|---|
| | | 0 | 3 | 7 | 18 | 24 | 48 |
| TP content [g/L] | 0.8-1.2 | 1.1 | 1.1 | 1.2 | 0.9 | 0.9 | 1.1 |
| HPSEC % aggregates >1200 kD | <5 | <5 | n.t. | <5 | n.t. | <5 | <5 |
| % fragments <100 kD | <5 | <5 | n.t. | <5 | n.t. | <5 | <5 |
| proteolytic activity (U/L) | <8 | <8 | n.t. | <8 | n.t. | <8 | <8 |

TABLE 7-continued

Stability study of a liquid Glu-plasminogen product
(Method 1. Lysine-Sepharose_glycine diafiltrated)
with specific product specifications.

| Parameters tested | Requirement (Tolerance) | Storage in hours at 37° C. | | | | | |
|---|---|---|---|---|---|---|---|
| | | 0 | 3 | 7 | 18 | 24 | 48 |
| Glu-plasminogen content (%) | >80% | 93% | 92% | 93% | 91% | 93% | 92% |

* ±10% Inter- and 5% intra-assay variations

Experimental Example 8—Mode-Of-Action Study

A new diagnostic study of patients with acute kidney failure demonstrates that a significant increase in the ratio of A2AP and PLG was detected in a control population (55 patients) and patients (25 patients) in the University Hospital of Mannheim.

Post-mortem studies of patients with sepsis demonstrate microvascular thrombi in many organs including the kidney, liver, lung, gut, adrenals and brain, and the degree of organ injury is related to the quantity of thrombi. For the analysis of organ failure, animal models of sepsis are used to demonstrate therapies, that inhibit coagulation or promote fibrinolysis, which reduce organ failure and mortality.

However, the usage of these sepsis-models leads to inconcrete analysis of the positive initiation of fibrinolysis. The mechanism of plasminogen cannot be defined in a complex disease model.

Four potential mode of action (MoA) models in preclinical experiments can define the treatment potential of Glu-plasminogen.

The question was, if Glu-plasminogen can initiate the fibrinolysis and will stabilize the balance between protein and inhibitor. It is proven which MoA is suitable.

2.1. Total Occlusion of V. Cava in a Murine Model (Prof. Anders University Munich).

Hypothesis (Found by Previous Experiments)

Intravenous injection of Glu-plasminogen has the potential of shifting the balance towards fibrinolysis to resolve the existing vein thrombus.

Short Overview

Process: During 3 days a deep vein thrombosis was built.

Analytic: The endpoint of the study→measurement of the clot size

| Advantages | Disadvantages |
|---|---|
| Established MoA model | Model for testing of coagulation and not for fibrinolysis |
| Easy to handle the occlusion of cava | Potential Lethal outcome before dosage optimization |
| Fast injury for many mice per day | |
| Defined endpoint of clot size | |

Material and Methods

In Vivo Experiment

Seven to eight-week-old male C57BL/6N mice were procured from Charles River Laboratories, Sulzfeld, Germany. They were maintained under standard housing conditions with free access to food and water. All animals underwent IVC ligation surgery and monitored for 72 h after surgery. All mice were sacrificed by cervical dislocation at the end of the study. All animal experiments were performed in accordance with the European protection laws of animal welfare, and with approval by the local government authorities Regierung von Oberbayern (reference number: 55.2-1-54-2532-54-2017).

| Test system | |
| --- | --- |
| Species | Mice. |
| Strain | C57BL/6N |
| Source | Charles River, Germany |
| Number on study | 12 mice in vehicle group and 9 in Glu-plasminogen group |
| Age/gender | 7 weeks male mice |
| Identification system | Animals were identified by marks on the tail. Individual cage cards were affixed to each cage, displaying details such as the animal number, the study number, the initiation dates and the experimenter |
| Justification for model selection | The animal model is a well-established, suitable model for the study of venous thrombosis model. |
| Husbandry Conditions | Standard laboratory conditions. Air conditioned with target ranges for room temperature of about 22 ± 4° C., for relative humidity of about 30-70% and approximately 10-15 air changes per hour. There was a 12-hour light/12-hour dark cycle. |
| Accommodation | Mice were kept in a group of 4 in cages with filter tops and standardized softwood bedding as enrichment as well as red-transparent houses. |
| Diet | Animals were fed on normal chow diet (Ssniff, Soest, Germany). The diet was available ad libitum. |
| Drinking water | Community tap water was supplied ad libitum by an automatic water dispenser. The quality of the drinking water was pursuant to the "Trinkwasserverordnung" (Directive in Potable Water) dated May 22, 1986, promulgation of the revised Directive on Jan. 1, 1991 in the German Federal Law Gazette I, no. 66, dated Dec. 12, 1990, pp 2 613-2 629 and amended in the German Federal Law Gazette I, no. 7, dated Feb. 8, 1991, p 227. |

Animal Receipt, Acclimatization and Monitoring

Qualified personnel inspected each animal upon receipt. Animals judged to be in good health and suitable as test animals were placed in quarantine for at least 1 week.

During acclimatization and biological phase of the study, animals were observed once daily for changes in general appearance and behavior.

Grouping and Treatment

Mice were randomized and assigned into two groups. Vehicle/PBS group (n=12) and Glu-plasminogen group (n=9 per group).

Surgery

All surgical procedures were carried out in sterile and designated area. Before surgery each animal was injected with 100 μl of narcosis and allowed the animals for 5-10 minutes into a 37° C. breeding chamber to undergo deep sleep. After 10 minutes, animal was taken out and placed on pre-heated (40° C.) heating plate so that the body temperature of the animal will be maintained during the surgery. 1-2 cm abdominal incision was made opened and inferior vena-cava (IVC) was located. Using 7-0 (8.0 mm0 mm 3/8 c8c) polypropylene monofilament non-absorbable suture (Prolene #8735H, Ethicon, Norderstedt, Germany) IVC was ligated (100% stenosis). After successful ligation, abdominal incision was closed and injected with 200 μL of antagonists and buprenorphine and place back again into a 37° C. breeding chamber and monitored for another one hour for any surgical complications.

Treatment Schedule

| | |
| --- | --- |
| Route of administration | Intravenous injection. |
| Frequency | One-time injection 15 h after surgery |
| Application volume | 180 μL total volume with 4.755 μg/mL concentration. |

Sacrifice

All animals were placed back into the animal facility and monitored and injected with 200 μl of Buprenorphin for every 12 h. All animal's stress conditions were recorded in a prescribed score sheets (Table 2). 72 hours after surgery all animals were sacrificed with cervical dislocation method. IVCs were dissected out and thrombus clot weights were measured and recorded.

Observations

Mortality and Clinical Signs

Animals were observed twice a day for any abnormal clinical signs and serious adverse events such as mortality.

Thrombus Formation and Resolution

Upon sacrifice individual animals were evaluated for thrombus formation (control animals) and resolution (treatment animals). Each individual animal thrombus weights were recorded and assessed for efficacy drug.

Results

Mortality

In the control group two animals and in Glu-plasminogen group one animal died due to surgical complications.

Thrombus Formation and Resolution

All vehicle-/PBS-treated group animals developed significant amount of thrombus clots, while almost all Glu-plasminogen-treated group animals showed no clot or maximum resolution of clot (Table 1 and FIGS. 1-5).

Discussion and Conclusions

The Glu-plasminogen produced according to this invention has surprisingly a high and excellent fibrinolytic activity. Therefore, we hypothesized that the product according to this invention will resolve the existing thrombus.

To test the hypothesis, we have used 100% stenosis of IVC in murine model venous thrombosis. Control mice with vehicle injection have shown development of thrombus clot formation after 72 h of stenosis. Compared with thrombus weights of vehicle mice, Glu-plasminogen group animals had no thrombus or significantly reduced thrombus weight after the administration of Glu-plasminogen extract. Therefore, the injection of Glu-plasminogen leads to no negative effect and shift the imbalance of coagulation and fibrinolysis to an increased fibrinolytic activity. In both groups mortality was observed due to surgical complications.

Therefore, we conclude that Glu-plasminogen developed has capabilities to initiate the fibrinolytic activity on this experimental venous thrombosis model.

TABLE 8

Table 1 showing the thrombus weight (in grams)

| Mouse No | Vehicle | Glu-plasminogen |
| --- | --- | --- |
| 1 | 0.0019 | 0.0012 |
| 2 | 0.0025 | 0.0019 |
| 3 | 0.0018 | 0.0000 |
| 4 | 0.0026 | 0.0000 |
| 5 | 0.0017 | 0.0000 |
| 6 | 0.0026 | 0.0000 |
| 7 | 0.0018 | 0.0000 |
| 8 | 0.0021 | 0.0000 |
| 9 | 0.0019 | dead |

TABLE 8-continued

Table 1 showing the thrombus weight (in grams)

| Mouse No | Vehicle | Glu-plasminogen |
|---|---|---|
| 10 | 0.0023 | |
| 11 | Dead | |
| 12 | Dead | |

Representative Graph of Thrombus Weights in Both Groups.

Thrombus weights were measured in grams. Data represent mean±SEM. p<0.0001 (n=10 vehicle group; n=8 treatment group). These data represent a highly significant (****) reduction of the already built thrombus after the injection of Glu-plasminogen.

Experimental Example 8.1. Transient Singular Ischemia-Reperfusion of the Kidney in a Murine Model Process: Ischemia-necrosis of renal tubules Analytic: Glomerular filtration rate (day 1 and 30), delta kidney weight (day 30), dimension of kidney fibrosis (day 30). Prof. Anders University Munich

| Advantages | Disadvantages |
|---|---|
| Kidney-model for further indication | Focus on ischemia of tubules |
| Renal health and general recovery after a time period | No experience with injury of glomerular and clot formation |
| | No definition of primary endpoint formation |
| | Long time period |
| | Not comparable with a disease or indication of a human patient |

Experimental Example 8.2. Kidney-Transplantation in a Murine-Model

Process: Analysis of the kidney rejection due to necrosis of kidney tissue and micro clot formation in capillaries.

Analytic: Glomerular filtration rate (day 1 and 30), delta kidney weight (day 30), dimension of kidney fibrosis (day 30) and clot formation. In contact.

| Advantages | Disadvantages |
|---|---|
| Established mode of action model Similar biochemical mechanism as a human transplantation Excellent comparable | Difficult to transplanted 1 or 2 mice per day, Long time period High costs No definition of primary endpoint formation |

Experimental Example 8.3. Graft Versus Host Disease (GvHD) in Murine Model

Process: bone marrow transplantation, leads to (GvHD) due to Von Willebrand factor activation and multimeric thrombocyte aggregation.

Analytic: The endpoint of the study→longer life time or not.

| Advantages | Disadvantages |
|---|---|
| Established mode of action model Easy for transplantation Fast injury Simulate most likely DIC | Complex disease Lethal outcome Difficult to analyze the success of treatment Many mechanism are influenced in the disease |

Experimental Example 9. Indication Opportunities for Glu-Plasminogen

In publications 30 years ago, it has been published that an increased ratio of alpha-2-antiplasmin (A2AP) and plasminogen (PLG) was detected in patients with cadaver kidney transplantation.

Furthermore, it was shown that the administration of plasminogen improved the physical conditions of patients with sepsis.

The imbalance of the high amount of alpha-2-antiplasmin and plasminogen shuts down the fibrinolytic activity and coagulation is not balanced. In a new diagnostic study of patients with acute kidney failure was shown that a significant ratio was detected between control population (55 patients) and patients (25 patients).

Raw-data: measurement of PLG and A2AP in patients with acute kidney failure. Normal range in the control population (55 healthy blood donors):
PLG: 82.7%-144.5%
A2AP: 96.9%-118.9%
ratio: 0.80-1.26
Results of the non-statistical normal distribution of 25 patients with acute renal failure:
1. 12/25 (48%) patients <82.67% PLG
2. 14/25 (56%) patients <96% A2AP
3. 6/25 (24%) patients >1.26 ratio (A2AP/PLG)
4. 4/25 (16%) patients >1.26 ratio and <82% PLG

| No. | Plasminogen [%] | α-2-Antiplasmin [%] | Ratio |
|---|---|---|---|
| 1 | 119.61 | 101.8 | 0.85 |
| 2 | 103.2 | 93.5 | 0.91 |
| 3 | 82.3 | 90.1 | 1.09 |
| 4 | 114.2 | 113 | 0.99 |
| 5 | 133.7 | 97.6 | 0.73 |
| 6 | 65.5 | 92.5 | 1.41 |
| 7 | 82.1 | 92.8 | 1.13 |
| 8 | 74.6 | 89.9 | 1.21 |
| 9 | 94.9 | 93.7 | 0.99 |
| 10 | 137.6 | 105.5 | 0.77 |
| 11 | 109.9 | 117.4 | 1.07 |
| 12 | 74.9 | 50.8 | 0.68 |
| 13 | 67.8 | 96.5 | 1.42 |
| 14 | 85.6 | 115.6 | 1.35 |
| 15 | 90.9 | 107.3 | 0.18 |
| 16 | 80.2 | 77.3 | 0.96 |
| 17 | 9.8 | 55.5 | 5.66 |
| 18 | 80.4 | 76.2 | 0.95 |
| 19 | 41.3 | 41.8 | 1.01 |

-continued

| No. | Plasminogen [%] | α-2-Antiplasmin [%] | Ratio |
|---|---|---|---|
| 20 | 77.3 | 99.3 | 1.28 |
| 21 | 125.5 | 115.7 | 0.92 |
| 22 | 92.1 | 84.8 | 0.92 |
| 23 | 123.1 | 114.3 | 0.93 |
| 24 | 77.8 | 98.5 | 1.27 |
| 25 | 108.1 | 67.5 | 0.62 |
| Mean | 90.10 | 91.56 | 1.21 |
| Std | 28.81 | 20.45 | 0.95 |
| Min | 9.80 | 41.80 | 0.62 |
| Max | 137.60 | 117.40 | 5.66 |
| Range | 127.80 | 75.60 | 5.04 |
| VK | 31.98% | 22.34% | 78.57% |
| Out of Normal Range | <82.67 | <96.925 | <0.8 |
| Number of Patients | 12 | 14 | 4 |
| Out of Normal Range | >144.45 | >118.9 | >1.26 |
| Number of Patients | 0 | 0 | 6 |
| Rest of Patients | 13 | 11 | 15 |

The study of acute kidney failure resulted in a significant difference between patients (Pat, suffering from acute kidney failure) and control group (NP, healthy individuals) in different parameters (rounded values):

|  | control group [55 individuals] | Patient [25 individuals] |
|---|---|---|
| alpha-2-antiplasmin (A2AP) | 107.7 ± 7.2 | 83.1 ± 4.1 |
| Glu-plasminogen (PLG) | 108.3 ± 18.8 | 78.2 ± 28.8 |
| A2AP/PLG [P = 0.16] | 1.02 ± 0.21 | 1.26 ± 0.95 |

Ongoing analysis of patients with acute kidney failure (AKI) resulted into a significant acquired plasminogen deficiency.

Study-Outline-Acute Kidney Failure (AKI)

Measurement of alpha-2-antiplasmin (A2AP) and Glu-plasminogen (PLG)

77 patients with acute renal failure (AKI)

53 control population (CP)

Result of t-Test-Mann Whitney Analysis:

A significant (**) acquired plasminogen deficiency in Patients with AKI

A significant (**) acquired alpha-2-antiplasmin deficiency in Patients with AKI

No significant difference of the ratio (A2AP/PLG)

Conclusion:

Patients with acute kidney failure (AKI) have in a high percentage an acquired plasminogen deficiency, i.e., an indication for a Glu-plasminogen substitution therapy.

TABLE 9

Mann Whitney analysis of plasminogen concentration.

| Table Analyzed | Data 1 |
|---|---|
| Column A | CP-plasminogen |
| Vs | vs |
| Column B | AKI-plasminogen |

TABLE 9-continued

Mann Whitney analysis of plasminogen concentration.

| Mann Whitney test | |
|---|---|
| P value | 0.0031 |
| Exact or approximate P value? | Gaussian approximation |
| P value summary | ** |
| Are medians signif. different? (P < 0.05) | Yes |
| One- or two-tailed P value? | Two-tailed |
| Sum of ranks in column A, B | 4096, 4420 |
| Mann-Whitney U | 1417 |

TABLE 10

Mann Whitney analysis of alpha-2-antiplasmin concentration.

| Table Analyzed | Data-2 |
|---|---|
| Column A | CP-alpha-2-antiplasmin |
| vs | vs |
| Column B | AKI-alpha-2-antiplasmin |
| Mann Whitney test | |
| P value | 0.0011 |
| Exact or approximate P value? | Gaussian approximation |
| P value summary | ** |
| Are medians signif. different? (P < 0.05) | Yes |
| One- or two-tailed P value? | Two-tailed |
| Sum of ranks in column A, B | 4160, 4355 |
| Mann-Whitney U | 1352 |

TABLE 11

Mann Whitney analysis of the ratio (A2AP/PLG).

| Table Analyzed | Data-3 |
|---|---|
| Column A | CP-ratio |
| vs | vs |
| Column B | AKI-ratio |
| Mann Whitney test | |
| P value | 0.1241 |
| Exact or approximate P value? | Gaussian approximation |
| P value summary | ns |
| Are medians signif. different? (P < 0.05) | No |
| One- or two-tailed P value? | Two-tailed |
| Sum of ranks in column A, B | 3147, 5369 |
| Mann-Whitney U | 1716 |

Experimental Example 9.1 Indication Disseminated Intravascular Coagulation (DIC)

Study-Outline-DIC:

Measurement of alpha-2-antiplasmin (A2AP), Glu-plasminogen (PLG), D-Dimer

21 Patients with DIC 53 control population

Result of Mann Whitney Analysis:

A significant (**) acquired plasminogen deficiency in patients with DIC

No acquired alpha-2-antiplasmin deficiency in patients with DIC

A significant (***) difference of the ratio (A2AP/PLG)

Conclusion:

Patients with DIC have in a high percentage an acquired plasminogen deficiency, i.e., an indication for a Glu-plasminogen substitution therapy.

TABLE 12

Mann Whitney analysis analysis of plasminogen concentration.

| | |
|---|---|
| Table Analyzed | PLG |
| Column A | CP-plasminogen |
| Vs | vs |
| Column B | DIC-plasminogen |
| Mann Whitney test | |
| P value | 0.0013 |
| Exact or approximate P value? | Gaussian approximation |
| P value summary | ** |
| Are medians signif. different? (P < 0.05) | Yes |
| One- or two-tailed P value? | Two-tailed |
| Sum of ranks in column A, B | 2256, 519 |
| Mann-Whitney U | 288.0 |

TABLE 13

Mann Whitney analysis analysis alpha-2-antiplasmin concentration.

| | |
|---|---|
| Table Analyzed | A2AP |
| Column A | CP-alpha-2-antiplasmin |
| vs | vs |
| Column B | DIC-alpha-2-antiplasmin |
| Mann Whitney test | |
| P value | 0.0730 |
| Exact or approximate P value? | Gaussian approximation |
| P value summary | ns |
| Are medians signif. different? (P < 0.05) | No |
| One- or two-tailed P value? | Two-tailed |
| Sum of ranks in column A, B | 2138, 637.5 |
| Mann-Whitney U | 406.5 |

TABLE 14

Mann Whitney analysis analysis of the ratio (A2AP/PLG).

| | |
|---|---|
| Table Analyzed | Ratio-DIC |
| Column A | CP-ratio |
| vs | vs |
| Column B | DIC-ratio |
| Mann Whitney test | |
| P value | <0.0001 |
| Exact or approximate P value? | Gaussian approximation |
| P value summary | *** |
| Are medians signif. different? (P < 0.05) | Yes |
| One- or two-tailed P value? | Two-tailed |
| Sum of ranks in column A, B | 1634, 1141 |
| Mann-Whitney U | 203.0 |

TABLE 15

Mann Whitney analysis analysis of plasminogen concentration.

| | |
|---|---|
| Table Analyzed | Sepsis-PLG |
| Column A | CP-plasminogen |
| vs | vs |
| Column B | Sepsis-plasminogen |
| Mann Whitney test | |
| P value | 0..0377 |
| Exact or approximate P value? | Gaussian approximation |
| P value summary | * |
| Are medians signif. different? (P < 0.05) | Yes |
| One- or two-tailed P value? | Two-tailed |
| Sum of ranks in column A, B | 1774, 179 |
| Mann-Whitney U | 134.0 |

TABLE 16

Mann Whitney analysis analysis alpha-2-antiplasmin concentration.

| | |
|---|---|
| Table Analyzed | Sepsis-A2AP |
| Column A | CP-alpha-2-antiplasmin |
| vs | vs |
| Column B | Sepsis-alpha-2-antiplasimin |
| Mann Whitney test | |
| P value | 0.0704 |
| Exact or approximate P value? | Gaussian approximation |
| P value summary | ns |
| Are medians signif. different? (P < 0.05) | No |
| One- or two-tailed P value? | Two-tailed |
| Sum of ranks in column A, B | 1761 , 192.5 |
| Mann-Whitney U | 147.5 |

TABLE 17

Mann Whitney analysis analysis of the ratio (A2AP/PLG).

| | |
|---|---|
| Table Analyzed | Sepsis-ratio |
| Column A | CP-ratio |
| vs | vs |
| Column B | Sepsis-ratio |
| Mann Whitney test | |
| P value | 0.2182 |
| Exact or approximate P value? | Gaussian approximation |
| P value summary | ns |
| Are medians signif. different? (P < 0.05) | No |
| One- or two-tailed P value? | Two-tailed |
| Sum of ranks in column A, B | 1608, 345.5 |
| Mann-Whitney U | 176.5 |

Experimental Example 9.2 Indication Sepsis

Study-Outline-Sepsis:

Measurement of alpha-2-antiplasmin (A2AP), Glu-plasminogen (PLG), PCTP

9 Patients 53 control population

Result of t-Test-Mann Whitney Analysis:

A significant (*) acquired plasminogen deficiency in Patients with Sepsis

No acquired Alpha-2-antiplasmin deficiency in Patients with Sepsis

No significant difference of the ratio (A2AP/PLG)

Conclusion:

Patients with sepsis have in a high percentage an acquired plasminogen deficiency, i.e., an indication for a Glu-plasminogen substitution therapy.

Overall Conclusion:

Acquired plasminogen deficiency is a highly complex disease, currently underdiagnosed due to fact that patients on risk are not tested for plasminogen and/or alpha-2-antiplasmin. The testing of these patients on risk may result in an indication for a Glu-plasminogen substitution therapy. Also, the testing of both parameters within the course of the disease should result in an indication for Glu-plasminogen.

The invention claimed is:

1. A method for isolating Glu-plasminogen, the method comprising the following steps:
    (i) providing a plasma fraction comprising Glu-plasminogen, wherein the plasma fraction is selected from the group consisting of:
        (a) cryo-poor plasma; and
        (b) fractions I+III of the Cohn or Kistler-Nitschmann process, fractions I+II+III of the Cohn or Kistler-Nitschmann process, or a combination thereof, wherein, optionally, octanoic acid is added to the fractions I+III or the fractions I+II+III;
(ii) contacting the plasma fraction with an anion exchanger based on a resin comprising cationic groups;
(iii) washing the anion exchanger obtained from step (ii) loaded with the plasma fraction with a first buffer B1 having a pH of 8.5 to 11 not comprising cations competing with the cationic groups of the resin of the anion exchanger;
(iv) eluting the Glu-plasminogen from the washed anion exchanger of step (iii) with a second buffer B2 having a pH of 8.5 to 11 comprising cations competing with the cationic groups of the resin of the anion exchanger, thereby obtaining a solution comprising the second buffer B2 and Glu-plasminogen;
(v) adjusting the pH of the solution obtained from step (iv) to a pH in a desired range of pH 4.5 to 6.5;
(vi) stabilizing the Glu-plasminogen by adding one or more stabilizers that prevent the Glu-plasminogen from maturing into plasmin and Lys-plasminogen to the solution obtained from step (iv) and/or step (v);
(vii) optionally subjecting the solution from any of steps (iv) to (vi) to one or more antiviral treatments; and
(viii) optionally drying or freeze-drying the solutions comprising Glu-plasminogen obtained from any of steps (iv) or (vii).

2. The method of claim 1, wherein the resin of the anion exchanger bears amino groups or salts thereof.

3. The method of claim 1, wherein the resin of the anion exchanger bears primary amino groups or salts thereof.

4. The method of claim 1, wherein the second buffer B2 comprises, as a cation competing with the cationic groups of the anion exchanger, a soluble amine or a salt thereof.

5. The method of claim 1, wherein the one or more stabilizers of step (vi) are selected from the group consisting of aprotinin, alpha-2-antiplasmin, D-phenylalanyl-L-prolyl-arginine chloromethyl ketone, small molecule stabilizers, and combinations thereof.

6. The method of claim 1, wherein the solution obtained from any of steps (iv) to (vi) is subjected to the one or more antiviral treatments of step (vii), wherein the one or more antiviral treatments are selected from the group consisting of:
(vii-a) adding one or more detergents;
(vii-b) adding one or more other antiviral agents other than detergents;
(vii-c) ultrafiltration; and
(vii-d) combinations of two or more thereof.

7. The method of claim 1, wherein the resin of the anion exchanger comprises amino groups having the structure moiety —R—$NH_2$ or —R—$NH_3^+$+$A^-$, wherein R is a $C_1$-$C_{10}$-alkylene residue and $A^-$ is an anionic counterion; wherein the cations in the second buffer B2 comprise a primary $C_1$-$C_{10}$-amine or a salt thereof competing with the amino groups of the anion exchanger; wherein the pH in the adjusting step (v) is in the range from 4.5 to 5.5; and wherein the method comprises subjecting the solution from any of steps (iv) to (vi) to the one or more antiviral treatments of step (vii).

8. The method of claim 7, wherein the one or more antiviral treatments comprise:
(vii-I) adding one or more detergents and one or more other antiviral agents;
(vii-II) removing the solution of step (vii-I); and
(vii-III) ultrafiltration.

9. The method of claim 1, wherein the resin of the anion exchanger comprises amino groups having the structure moiety —R—$NH_2$ or —R—$NH_3$++$A^-$, wherein R is a $C_1$-$C_{10}$-alkylene residue and $A^-$ is an anionic counterion; wherein the first buffer B1 comprises a buffer agent at a concentration from 0.01 to 0.1M; and wherein the second buffer B2 comprises a buffer agent at a concentration from 0.01 to 0.1M, and the cations in the second buffer B2 comprises a primary $C_1$-$C_{10}$-amine or a salt thereof competing with the amino groups of the anion exchanger.

* * * * *